(12) United States Patent
Takeuchi

(10) Patent No.: US 7,217,243 B2
(45) Date of Patent: May 15, 2007

(54) ULTRASOUND DIAGNOSIS APPARATUS

(75) Inventor: Hideki Takeuchi, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 342 days.

(21) Appl. No.: 10/869,152

(22) Filed: Jun. 16, 2004

(65) Prior Publication Data

US 2004/0267135 A1   Dec. 30, 2004

(30) Foreign Application Priority Data

Jun. 25, 2003 (JP) ............. 2003-181070
Jun. 25, 2003 (JP) ............. 2003-181104

(51) Int. Cl.
    *A61B 8/00* (2006.01)
(52) U.S. Cl. ................... 600/447
(58) Field of Classification Search ........ 600/437, 600/440–441, 443, 447, 455–458; 128/916; 73/625–626
    See application file for complete search history.

(56) References Cited

U.S. PATENT DOCUMENTS

| | | | |
|---|---|---|---|
| 5,229,933 A | 7/1993 | Larson, III | |
| 5,349,262 A | 9/1994 | Grenon et al. | |
| 5,563,346 A | 10/1996 | Bartelt et al. | |
| 5,617,862 A | 4/1997 | Cole | |
| 5,832,923 A | 11/1998 | Engeler et al. | |
| 5,897,501 A | 4/1999 | Wildes et al. | |
| 5,997,479 A * | 12/1999 | Savord et al. | 600/447 |
| 6,013,032 A * | 1/2000 | Savord | 600/443 |
| 6,089,096 A | 7/2000 | Alexandru | |
| 6,102,863 A * | 8/2000 | Pflugrath et al. | 600/447 |
| 6,111,816 A | 8/2000 | Chiang et al. | |
| 6,174,286 B1 * | 1/2001 | Ramamurthy et al. | 600/447 |
| 6,193,663 B1 * | 2/2001 | Napolitano et al. | 600/447 |
| 6,375,617 B1 * | 4/2002 | Fraser | 600/443 |
| 6,491,634 B1 * | 12/2002 | Leavitt et al. | 600/447 |
| 6,537,219 B2 * | 3/2003 | Poland et al. | 600/447 |
| 6,540,862 B1 * | 4/2003 | Calvert et al. | 156/244.17 |
| 6,582,367 B1 * | 6/2003 | Robinson et al. | 600/443 |
| 6,868,729 B2 * | 3/2005 | Amemiya | 73/626 |
| 2003/0018260 A1 | 1/2003 | Erikson | |

FOREIGN PATENT DOCUMENTS

| | | |
|---|---|---|
| JP | 9-322896 | 12/1997 |
| JP | 2001-104303 | 4/2001 |
| JP | 2001-276064 | 10/2001 |

* cited by examiner

*Primary Examiner*—Francis J. Jaworski
(74) *Attorney, Agent, or Firm*—Koda & Androlia

(57) ABSTRACT

A plurality of 2D sub arrays are defined on a 2D array transducer for effecting transmission and reception of ultrasound. For each sub array, a plurality of groups are set. More specifically, a plurality of (16, for example) transducer elements forming a sub array are grouped or divided into a plurality of (4, for example) groups. A multiplexer sums a plurality of receiving signals output from the plurality of transducer elements for each group, and generates a group receiving signal. A plurality of group receiving signals thus generated are then subjected to a sub phase adjusting and summing process to form a sub phase adjusted and summed signal. A plurality of sub phase adjusted and summed signals corresponding to the plurality of sub arrays are then subjected to a main phase adjusting and summing process. A sub phase adjusting and summing processing section is provided within a probe head, a cable connector, or an apparatus body. During transmission, the multiplexer supplies a transmitting signal to a plurality of transducer elements forming a group in parallel.

14 Claims, 17 Drawing Sheets

| TRANSMITTING BEAM ADDRESS | SUB ARRAY #1 | | SUB ARRAY #2 | |
| --- | --- | --- | --- | --- |
| | GROUPING PATTERN | SET OF TRANSMITTING DELAY AMOUNT SET OF RECEIVING SUB DELAY AMOUNT | GROUPING PATTERN | SET OF TRANSMITTING DELAY AMOUNT SET OF RECEIVING SUB DELAY AMOUNT |
| 1 | A1 | | A2 | |
| 2 | B1 | | B2 | |
| 3 | C1 | | C2 | |

ULTRASOUND DIAGNOSIS APPARATUS

BACKGROUND OF THE INVENTION

1. Field of the Invention

The present invention relates to an ultrasound diagnosis apparatus for use in the field of medical treatment, and more particularly to a channel reduction technology.

2. Description of Related Art

Ultrasound diagnosis apparatuses are used in the field of medical treatment for the purpose of diagnosing diseases of a living body (patient). More specifically, ultrasonic diagnosis apparatuses transmit an ultrasonic pulse to a living body and receive a reflected wave therefrom for forming an ultrasonic image based on a receiving signal obtained by the reflected wave received. A typical ultrasonic diagnosis apparatus includes an apparatus body (main unit) and a probe (probe unit) connected to the apparatus body. The probe generally includes a probe head, a cable, and a connector.

An array transducer (transducer array) provided within the probe head is composed of a plurality of transducer elements. There is a recent trend of forming the array transducer by a multiple elements. A variety of 2D array transducers which effect two-dimensional scanning of an ultrasonic wave to form a three dimensional space are put into practical use. Among them are 2D array transducers including several thousand transducer elements.

When a signal line is provided independently for each of the transducer elements forming an array transducer, a great number of signal lines must be connected for the array transducer as a whole. In such a structure, the diameter of a probe cable (a cable which encases a plurality of signal lines) extended from the probe head becomes very large, and the number of terminals (pins) of the connector provided at the end of the probe cable is also increased. In addition, because it is necessary to provide a transmitter and a receiver for each transducer element, the transmitter section and the receiver section will have an increased circuit scale. Accordingly, with the development of array transducers including multiple transducer elements, there has been a demand that the diameter of the probe cable and the number of channels (the number of transmitters and receivers) both be reduced.

Japanese Patent Laid-Open Publication No. 2001-104303 discloses a structure in which a plurality of transducer elements are fixedly connected to a single common signal line (See FIGS. 2 and 4 of the publication). Japanese Patent Laid-Open Publication No. 2001-276064 discloses a structure in which two phase-adjusting and summing circuits (or beam forming circuits) are provided in stages. Japanese Patent Laid-Open Publication No. Hei 9-322896 discloses, in FIG. 6, that a plurality of groups are fixedly set for a 2D array transducer, that a plurality of first beam formers are connected to the plurality of groups, and that a plurality of second beam formers are provided at the subsequent stage of the plurality of first beam formers. None of these documents, however, describes that a plurality of groups are dynamically set for each of sub arrays provided on the 2D array transducer, or that channel reduction is performed using each of these groups. U.S. Pat. No. 5,832,923 discloses that a plurality of 2D sub arrays are defined on a 2D array transducer and that a plurality of groups are defined on each sub array. In this patent, however, the number of transducer elements forming each group is identical among a plurality of groups. Accordingly, this document does not describe the feature of varying the number of transducer elements forming each group in accordance with the beam direction.

SUMMARY OF THE INVENTION

The present invention advantageously provides an ultrasound diagnosis apparatus to which a new and preferable method concerning channel reduction is applied.

The present invention also advantageously provides an ultrasound diagnosis apparatus in which a thin probe cable can be used.

The present invention also advantageously enables reduction of side lobes which lowers the quality of an ultrasonic image.

(1) An ultrasound diagnosis apparatus in accordance with one aspect of the present invention comprises (a) an array transducer composed of a plurality of transducer elements which are divided into a plurality of sub arrays, (b) a group setting section for setting a plurality of groups with respect to a plurality of transducer elements within each sub array in accordance with a beam forming condition, the group setting section being capable of varying the number of transducer elements forming each group, (c) a transmitter section for supplying a plurality of transmitting signals to the plurality of groups which are set with respect to each sub array, and (d) a receiver section for processing a plurality of group receiving signals corresponding to the plurality of groups which are set with respect to each sub array.

With the above structure, a plurality of sub arrays are defined with respect to the array transducer, and a plurality of groups are defined with respect to each sub array. When a certain group is formed by a plurality of transducer elements, a common transmitting signal is supplied to these transducer elements. Further, when a group is formed by a plurality of transducer elements, a plurality of receiving signals output from the plurality of transducer elements are combined to thereby form a group receiving signal. Consequently, the number of transmitting signals to be generated by the transmitter section (transmitting means) and the number of receiving signals to be processed by the receiver section (receiving means) can be reduced. In other words, channel reduction can be achieved simply.

The sub array pattern on the array transducer is fixedly defined or is dynamically variable. Each group is normally formed by a plurality of transducer elements. However, a group which is formed by a single transducer element may exist among a plurality of groups. It is desirable to adaptively vary the form of a plurality of groups (grouping pattern) in accordance with the beam forming condition (such as the beam scanning direction and the required beam profile, for example). In such a case, it is desirable to adaptively set the number of transducer elements forming a group. Preferably, the array transducer is a 2D array transducer, and each sub array is a 2D sub array. The receiver section may be composed of a sub section and a main section. Similarly, the transmitter section may be composed of a sub section and a main section. All the transducer elements within each sub array may be utilized as effective transducer elements (i.e. transducer elements effecting transmission and reception of ultrasound), or one or a plurality of ineffective transducer elements (i.e. transducer elements not effecting transmission and reception of ultrasound) may be defined for all or a part of the sub arrays.

Preferably, the group setting section includes a switching circuit, and the switching circuit sums a plurality of receiving signals for each group to perform receiving channel reduction at the time of receiving and outputs an identical transmitting signal to a plurality of transducer elements for each group in parallel to perform transmitting channel reduction at the time of transmitting.

Preferably, the switching circuit is a switching matrix circuit for selectively connecting a plurality of transducer elements within each sub array with a plurality of group signal lines. The switching matrix circuit connects each transducer element within each sub array to a group signal line selected from the plurality of group signal lines and the switching matrix circuit is capable of connecting a desired number of transducer elements to each group signal line. With this structure, a plurality of group signal lines are generally formed by the number of signal lines which is the same as the number of groups which are set on each sub array. Preferably, the switching matrix circuit has a great number of switches respectively provided at intersections between a plurality of group signal lines and a plurality of signal lines extended from a plurality of transducer elements. With the ON/OFF operation of these switches, grouping is performed.

Preferably, the switching matrix circuit varies the number of transducer elements connected to each group signal line in accordance with the beam forming condition. Preferably, a plurality of transducer elements forming each sub array are classified into a plurality of effective transducer elements and one or a plurality of ineffective transducer elements in accordance with the beam forming condition, and the plurality of effective transducer elements are connected with the plurality of group signal lines. Preferably, means for performing weighting with respect to each of the group receiving signals in accordance with the number of transducer elements forming each group is further provided.

Preferably, the array transducer and the group setting section are provided within the probe head. Preferably, the transmitter section is further provided within the probe head. With this structure, the number of a plurality of signal lines forming the probe cable can be reduced.

Preferably, the receiver section includes a plurality of sub phase adjusting and summing circuits provided corresponding to the plurality of sub arrays, each sub phase adjusting and summing circuit performing a sub phase adjusting and summing process with respect to a plurality of group receiving signals to output a sub phase adjusted and summed signal, and at least one main phase adjusting and summing circuit for performing a main phase adjusting and summing process with respect to a plurality of sub phase adjusted and summed signals output from the plurality of sub phase adjusting and summing circuits.

With the above structure, after the sub phase adjusting and summing process is performed for each sub array, the main phase adjusting and summing process is performed with respect to a plurality of sub phase adjusted and summed signals. The number of signals is decreased stepwise through a plurality of stages including grouping, sub phase adjusting and summing, and main phase adjusting and summing as described above, and finally, one signal (a main phase adjusted and summed signal) is obtained for one receiving beam. Here, a phase adjusting and summing process (or a beam forming process) refers to a process in which each of a plurality of signals is first phase-adjusted (delayed) and then the resultant signals are added together.

Preferably, the array transducer, the group setting section, and the plurality of sub phase adjusting and summing circuits are provided within the probe head. With this structure, the number of signal lines forming the probe cable can be further reduced.

Preferably, the receiver section further includes a plurality of main phase adjusting and adding circuits, so that a plurality of receiving beams can be formed simultaneously by one receiving process. Simultaneous formation of a plurality of receiving beams allows increase in the frame rate or volume rate. Even when a plurality of receiving beams are formed, an individual sub phase adjusting and summing circuit or the like can be shared among a plurality of receiving beams.

Preferably, the group setting section includes a plurality of switching circuits which are provided corresponding to the plurality of sub arrays, and each switching circuit groups m transducer elements within each sub array into n (1<n<m) groups. Here, the number m of transducer elements within a sub array (or the number m of effective transducer elements within a sub array), the number n of groups for each sub array, and the number k of sub arrays which will be described below are integers having a relationship of 1<n<m, and k is 2 or greater.

Preferably, the group setting section dynamically changes a group setting pattern for each sub array in accordance with a beam scanning direction which is given as the beam forming condition. Preferably, the change of a group setting pattern includes changing the number of transducer elements forming each group and changing a shape of each group. Preferably, the change of a group setting pattern further includes changing whether or not one or a plurality of ineffective transducer elements are included in each sub array.

The group setting section (or the group setting means) is preferably formed by a switching circuit such as a multiplexer and a switching matrix. A plurality of receiving signals supplied from a plurality of transducer elements are simply added (wired addition) on group units on the group setting section by means of electrical connection of a plurality of signal lines. However, weighted addition or the like may be performed as necessary.

(2) An ultrasound diagnosis apparatus in accordance with another aspect of the present invention comprises (a) a probe head, (b) an array transducer provided within the probe head and formed by a plurality of transducer elements which are divided into k (1<k) sub arrays, (c) a group setting section provided within the probe head for setting n groups with respect to m transducer elements within each of the sub arrays, where 1<n<m, in accordance with a beam forming condition, the group setting section being capable of varying the number of transducer elements forming each group, (d) transmitter circuits, the number of the transmitter circuits being k, provided corresponding to the k sub arrays within the probe head, each transmitter circuit supplying n transmitting signals to n groups which are set for the corresponding sub array, and (e) sub phase adjusting and summing circuits, the number of the sub phase adjusting and summing circuits being k, provided corresponding to the k sub arrays within the probe head, each sub phase adjusting and summing circuit performing a sub phase adjusting and summing process with respect to n group receiving signals and outputting a sub phase adjusted and summed signal.

Preferably, one or a plurality of main phase adjusting and summing circuits are further provided for performing a main phase adjusting and summing process with respect to k sub phase adjusted and summed signals output from the k sub phase adjusting and summing circuits. Preferably, the group setting section sums a plurality of receiving signals output from a plurality of transducer elements forming a group to generate a group receiving signal at the time of receiving, and supplies an identical transmitting signal in parallel to the plurality of transducer elements forming the group at the time of transmitting. Preferably, the group setting section includes a switching matrix circuit, and the switching matrix circuit is capable of connecting a desired number of transducer elements with one group signal line.

(3) An ultrasound diagnosis apparatus in accordance with still another aspect of the present invention comprises (A) a first unit, which serves as a probe head, and (B) a second unit connected to the first unit via a probe cable, the first unit including (a) an array transducer formed by a plurality of transducer elements which are divided into a plurality of sub arrays, and (b) a group setting section for setting a plurality of groups with respect to a plurality of transducer elements within each of the sub arrays in accordance with a beam forming condition, the group setting section being capable of varying the number of transducer elements forming each group, and the second unit including (c) a transmitter section for supplying a plurality of sets of transmitting signals to the group setting section via the probe cable, and (d) a receiver section for processing a plurality of sets of group receiving signals supplied from the group setting section via the probe cable.

With the above structure, a plurality of sub arrays are defined with respect to the array transducer, and a plurality of groups are defined with respect to each sub array. When a certain group is formed by a plurality of transducer elements, a common transmitting signal is supplied to these transducer elements. Further, when a group is formed by a plurality of transducer elements, a plurality of receiving signals output from the plurality of transducer elements are combined to thereby form a group receiving signal. Consequently, the number of transmitting signals to be generated by the transmitter section and the number of receiving signals to be processed by the receiver section can be reduced. In other words, channel reduction can be simply achieved. By varying the number of transducer elements forming each group in accordance with the beam forming condition, a preferable ultrasonic beam can be formed. One or a plurality of ineffective transducer elements may be defined within each sub array in accordance with the beam forming condition.

The second unit corresponds to a connector of the probe cable and the apparatus body, or the apparatus body. In the former case, a part of or a whole of the transmitter section, or a part of or a whole of the receiver section may be provided within the connector.

Preferably, the receiver section includes a plurality of sub phase adjusting and summing circuits provided corresponding to the plurality of sub arrays, each sub phase adjusting and summing circuit performing a sub phase adjusting and summing process with respect to a set of group receiving signals input thereto and outputting a sub phase adjusted and summed signal, and a main phase adjusting and summing circuit for performing a main phase adjusting and summing process with respect to a plurality of sub phase adjusted and summed signals output from the plurality of sub phase adjusted and summed circuits.

With the above structure, after the sub phase adjusting and summing process is performed for each sub array, the main phase adjusting and summing process is performed with respect to a plurality of sub phase adjusted and summed signals. The number of signals is decreased stepwise through a plurality of stages including grouping, sub phase adjusting and summing, and main phase adjusting and summing as described above, and finally, one signal (a main phase adjusted and summed signal) is obtained for one receiving beam.

Preferably, the second unit comprises a cable connector and an apparatus body, and at least the plurality of sub phase adjusting and summing circuits are contained within the cable connector. Preferably, the transmitter section is further provided within the cable connector. When the sub phase adjusting and summing and generation of transmitting signal is performed within the cable connector, it is also possible to perform three-dimensional ultrasonic diagnosis by connecting the cable connector to the probe connecting portion provided in the apparatus body in a conventional ultrasound diagnosis apparatus.

Preferably, the second unit comprises an apparatus body, and the transmitter section and the receiver section are provided within the apparatus body.

Preferably, the group setting section includes a plurality of switching circuits for grouping m transducer elements within each sub array into n groups, where $1<n<m$. Here, the number m of transducer elements forming a sub array, the number n of groups for each sub array, and the number k of sub arrays which will be described below are integers having a relationship of $1<n<m$, and k is 2 or greater.

Preferably, each of the m transducer elements is an effective transducer element, and each sub array includes one or a plurality of ineffective transducer elements in addition to the m effective transducer elements in accordance with the beam forming condition.

Preferably, between the first unit and the second unit, a transmitting signal is transmitted as a voltage signal and a receiving signal is transmitted as a current signal. The transmitting signal may be an approximately 100V signal or a low voltage type signal with approximately several V to several tens V. In the latter case, because each transducer element is preferably of a low impedance type, a lamination method, for example, is used in manufacturing of the array transducer. When a receiving signal is a current signal, problems of signal attenuation and degradation of frequency characteristics caused by the capacitance of the signal line can be eliminated or reduced. A two-way transmission circuit (an input-output circuit) may be provided on both ends of the signal line, or on the end of the signal line at the apparatus side.

Preferably, each of the sub phase adjusting and summing circuits is an analog phase adjusting and summing circuit including a delay line. Preferably, each of the sub phase adjusting and summing circuits is a digital phase adjusting and summing circuit. Preferably, each of the sub phase adjusting and summing circuit is a phase adjusting and summing circuit including a CCD.

(4) An ultrasound diagnosis apparatus in accordance with a further aspect of the present invention comprises (A) a first unit, which serves as a probe head, and (B) a second unit connected to the first unit via a group of signal lines, the first unit including (a) an array transducer formed by a plurality of transducer elements which are divided into k ($1<k$) sub arrays, and (b) a group setting section for setting n groups with respect to m transducer elements within each of the sub arrays in accordance with a beam forming condition, where $1<n<m$, the group setting section being capable of varying the number of transducer elements forming each group, and the second unit including (c) a transmitter section for supplying k sets of transmitting signals to the group setting section via the group of signal lines, and (d) a receiver section for processing k sets of grouping receiving signals supplied from the group setting section via the group of signal lines, wherein (e) each set of transmitting signals is formed by n transmitting signals, and (f) each set of group receiving signals is formed by n group receiving signals.

BRIEF DESCRIPTION OF THE DRAWINGS

Preferred embodiments of the present invention will be described in further detail based on the following drawing, wherein:

FIG. 9 is a view showing a relationship between the transmitting beam address and operation conditions determined for each sub array;

DETAILED DESCRIPTION OF PREFERRED EMBODIMENTS

Preferred embodiments of the present invention will be described with reference to the accompanying drawings. FIGS. 1 to 10 and FIGS. 18 to 20 show a first embodiment, and FIGS. 11 to 17 show second and third embodiments. FIGS. 3 to 10 and FIGS. 19 and 20 will also be referred to for the purpose of understanding the second and third embodiments. In other words, the same channel reduction method is applied to each embodiment.

Figure 18:
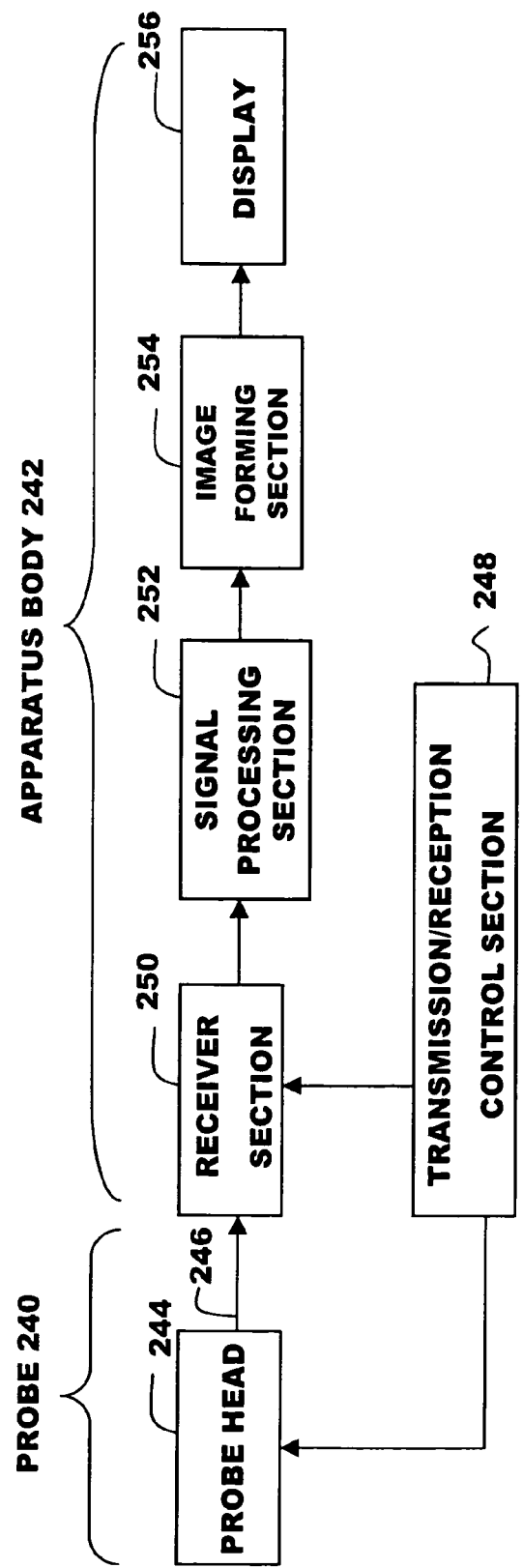
FIG. 18 is a block diagram showing a whole structure of an ultrasound diagnosis apparatus of the present invention.

Referring first to FIG. 18, a basic structure of an ultrasound diagnosis apparatus according to a first embodiment of the present invention will be described. The ultrasound diagnosis apparatus is composed of a probe (probe unit) 240 and an apparatus body 242. The probe 240 includes a probe head 244, a probe cable 246, and a cable connector (not shown). The apparatus body 242 includes a transmission/reception control section 248, a receiver section 250, a signal processing module 252, an image forming section 254, and a display 256. The probe head 244 transmits and receives ultrasound. A receiving signal, which is obtained by transmission and reception of ultrasound, is then input to the image forming section 254 through the receiver section 250 and the signal processing module 252. The image forming section 254 forms an ultrasonic image based on the signal received. The ultrasonic image is displayed on the screen of the display 256. Two-dimensional tomography images, two-dimensional blood stream images, and three-dimensional images are among the images collectively known as ultrasonic images. In the present embodiment, volume data obtained from a three-dimensional space within a living body is subjected to a volume rendering process to form a three-dimensional image. Many other methods for forming a three-dimensional image are also known.

Figure 1:
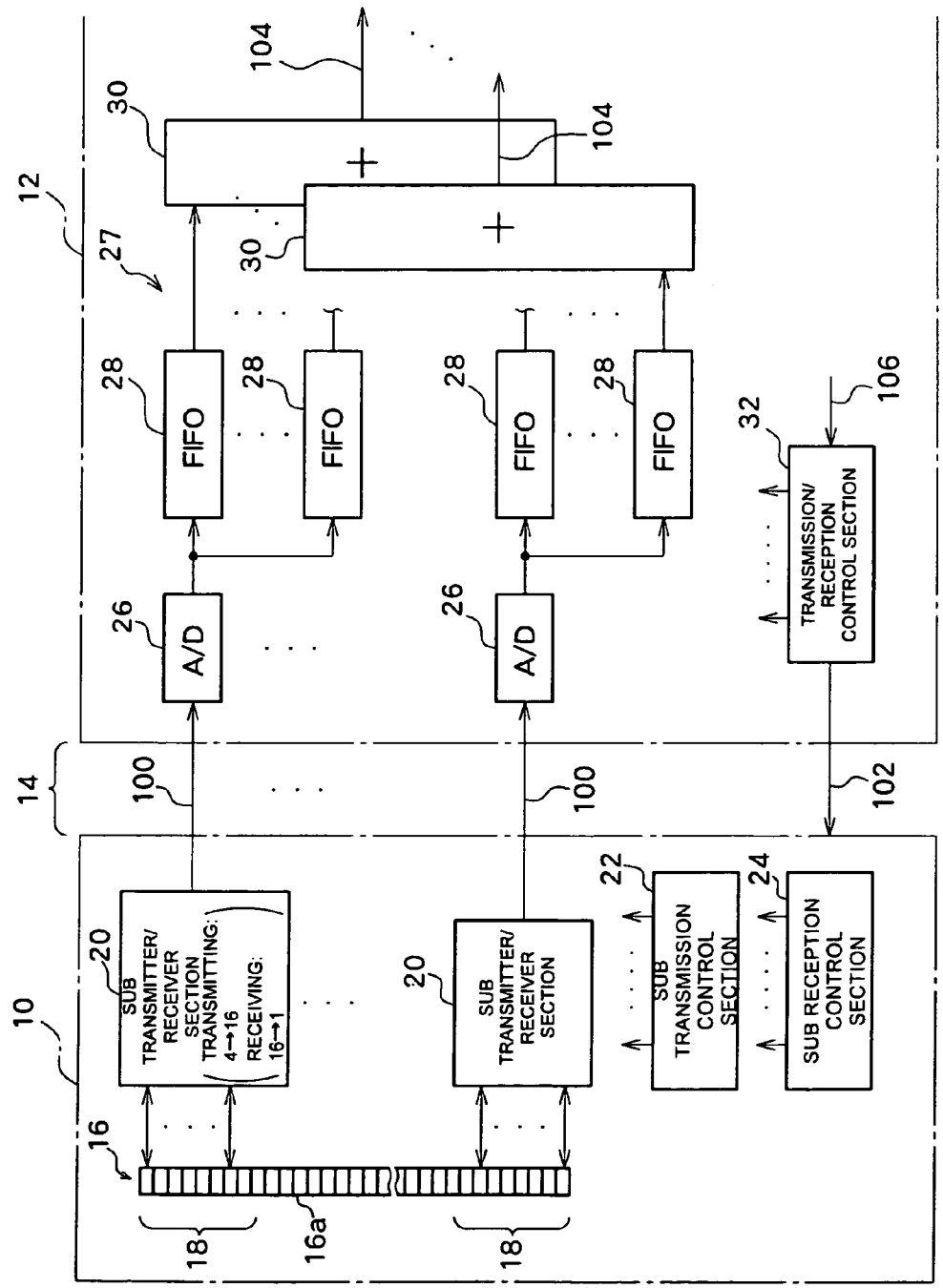
FIG. 1 is a block diagram showing a first embodiment of an ultrasound diagnosis apparatus of the present invention.

FIG. 1 is a block diagram showing a structure of a principle portion in the first embodiment. As described above with reference to FIG. 18, an ultrasound diagnosis apparatus is composed of a probe unit and an apparatus body 12. The probe unit includes a probe head 10, a probe cable 14, and a cable connector which is not shown. The cable connector is detachably connected to the apparatus body 12, which is provided with a connector for a probe connector.

The probe head 10 is used in contact with a surface of a living body, for example, and transmits an ultrasonic pulse and receives a reflected wave thereof in such a contact state. The probe head 10 includes a 2D (two-dimensional) array transducer 16 which is composed of a plurality of transducer elements 16a arranged two-dimensionally. The 2D array transducer 16 generates an ultrasonic beam, which is electronically scanned in a two-dimensional manner. The electronic scanning method in this case includes electronic sector scanning, electronic linear scanning, and on the like. With the two-dimensional electronic scanning of an ultrasonic beam, a three-dimensional space (three-dimensional echo data acquiring space) is formed. In the present embodiment, the 2D array transducer 16 is composed of approximately four thousand transducer elements 16a.

A plurality of 2D sub arrays are defined with respect to the 2D array transducer 16 (which will be further described with reference to FIG. 3). These sub arrays 18 are defined such that they are closely connected with each other on the 2D array transducer 16. In the present embodiment, a plurality of sub arrays have a rectangular shape. Although the position and the shape of each sub array are fixedly determined, they may be adaptively changed.

The probe head 10 contains a plurality of sub transmitter/receiver (transceiver) sections 20. In the present embodiment, the sub arrays 18 and the sub transmitter/receiver sections 20 correspond to each other on a one-to-one basis. In the present embodiment, for example, 128 sub arrays are provided and 128 sub transmitter/receiver sections 20 are provided correspondingly. As will be further described below with reference to FIG. 2 or the like, each sub transmitter/receiver section 20 of the present-embodiment is provided with a group setting function, a sub phase adjusting and summing function, and a transmitting signal generating function. With the group setting function, a plurality of transducer elements (e.g., 16 transducer elements) 16a forming a sub array 18 are grouped or divided into a plurality of groups (e.g., 4 groups). Each group includes a plurality of transducer elements (or a single transducer element as an exception). In the present embodiment, the number of transducer elements forming each group is variably set in accordance with the beam forming condition (particularly, the beam scanning direction, the beam deflecting (steering) direction, or beam shape). In other words, while the setting pattern for a plurality of sub arrays is fixed, the setting pattern for a plurality of groups within each sub array is variable. By varying the number of transducer elements forming each group in accordance with the beam forming condition, side lobe can be reduced or a preferable beam profile can be obtained.

Figure 2:
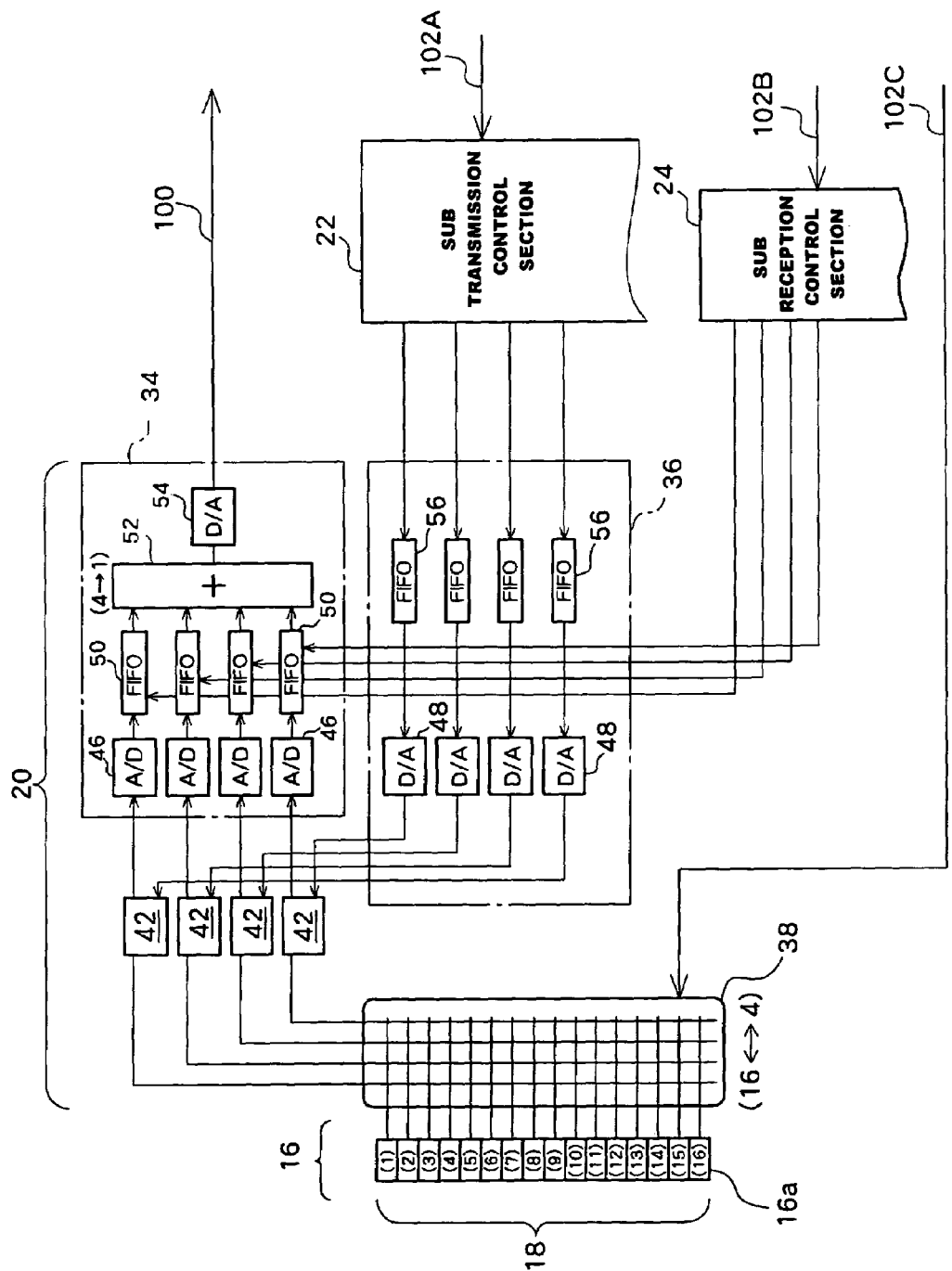
FIG. 2 is a circuit diagram showing an example structure of a sub transmitter/receiver section of FIG. 1.

With the above grouping, at the time of transmitting, a single transmitting signal, which is supplied on group units, is supplied to one or a plurality of transducer elements forming a specific one group corresponding to the transmitting signal. Normally, one group is composed of two or more transducer elements, and a single transmitting signal is therefore supplied to the two or more transducer elements in parallel. At the time of receiving, on the other hand, a single group receiving signal is obtained for each group. Because one group is normally composed of two or more transducer elements, a group receiving signal output from a multiplexer, which will be described below with reference to FIG. 2, is obtained by adding two or more receiving signals output from two or more transducer elements. In the present embodiment, addition (summing) of a plurality of receiving signals obtained for each group is performed by connection of a plurality of signal lines in a multiplexer. More specifically, a plurality of receiving signals are added together due to interconnection of a plurality of signal lines extended from a plurality of transducer elements, whereby a single group receiving signal is obtained. In such a case, it is, of course, possible to perform weighted addition of a plurality of receiving signals or the like. In accordance with the beam forming condition, one or a plurality of transducer elements within the sub array may be provided as ineffective transducer elements (i.e., a transducer element to which the group signal line is not connected). In such a case, a plurality of effective transducer elements (a transducer element to which the group signal line is connected) within the sub array are used to form a plurality of groups.

As can be understood from the above description, with the grouping function of each sub transmitter/receiver section 20, channel reduction is achieved for each sub array. For example, as a result of grouping 16 transducer elements into 4 groups, a channel reduction ratio of 1/4 can be realized. In addition, each sub transmitter/receiver section 20 is also provided with a sub phase adjusting and summing function as described above, and can achieve channel reduction using this function. More specifically, 4 group receiving signals, for example, obtained for each sub array 18 are subjected to a phase adjusting and summing process within the probe head 10, whereby a single sub phase adjusted and summed signal is obtained for each sub array 18. In other words, when focusing attention on the process of a receiving signal, while 16 receiving signals generated by 16 transducer elements are initially obtained for each sub array, each sub transmitter/receiver sections 20 outputs only a single receiving signal (a sub phase adjusted and summed signal). This results in a channel reduction ratio of 1/16 with regard to the receiving process in the probe head 10. As will be described below, each sub transmitter/receiver section 20 includes the number of transmitters (4 transmitters, for example) corresponding to the number of groups forming a sub array. Accordingly, at the time of transmitting, 16 transducer elements, for example, are driven by 4 transmitting signals, for example. Specifically, a single transmitting signal is generated for one group, and thus 4 transmitting signals are supplied to 4 groups (that is, 16 transducer elements forming the sub array). Here, a channel reduction ratio of 1/4 is achieved.

The probe head 10 has a sub transmission control section 22 for controlling the transmitting operation in the plurality of sub transmitter/receiver sections 20. Further, the probe head 10 also has a sub reception control section 24 for controlling the receiving signal process in the plurality of sub transmitter/receiver sections 20. These control sections will be described in further detail below. A probe cable 14 including a plurality of signal lines 100 and one or a plurality of control lines 102 is provided between the probe head 10 and the apparatus body 12. Each signal line 100 is connected to a specific sub transmitter/receiver section 20.

The structure of the apparatus body 12 will be described. A plurality of (128, for example) sub phase adjusted and summed signals which are output as analog signals as will be described below, are input to a plurality of (128, for example) A/D converters 26, respectively, where each input signal is converted into a digital signal. Output signals from the respective A/D converters 26 are stored in parallel in a plurality of FIFO (first-in first-out) memories 28 which are disposed in parallel with each other. In the present embodiment, 16 FIFO memories 28 are provided for each sub array 18 so as to form 16 receiving beams simultaneously by one receiving process. Reading control with respect to each FIFO memory 28 is performed by a transmission/reception control section 32 which will be described below. The transmission/reception control section 32 determines a delay amount by controlling the reading timing with respect to each FIFO memory 28.

Figure 11:
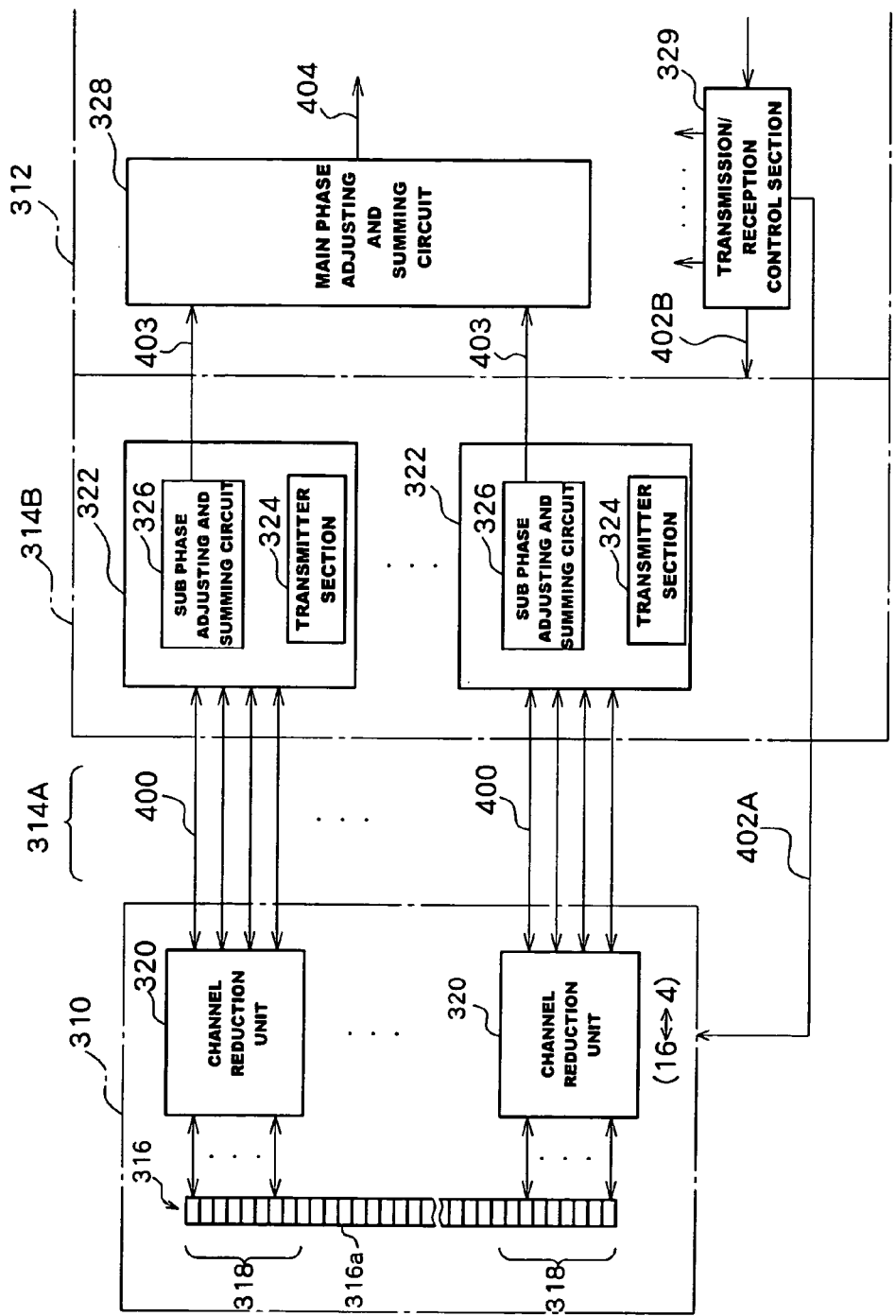
FIG. 11 is a block diagram showing a second embodiment of an ultrasound diagnosis apparatus of the present invention.
Figure 12:
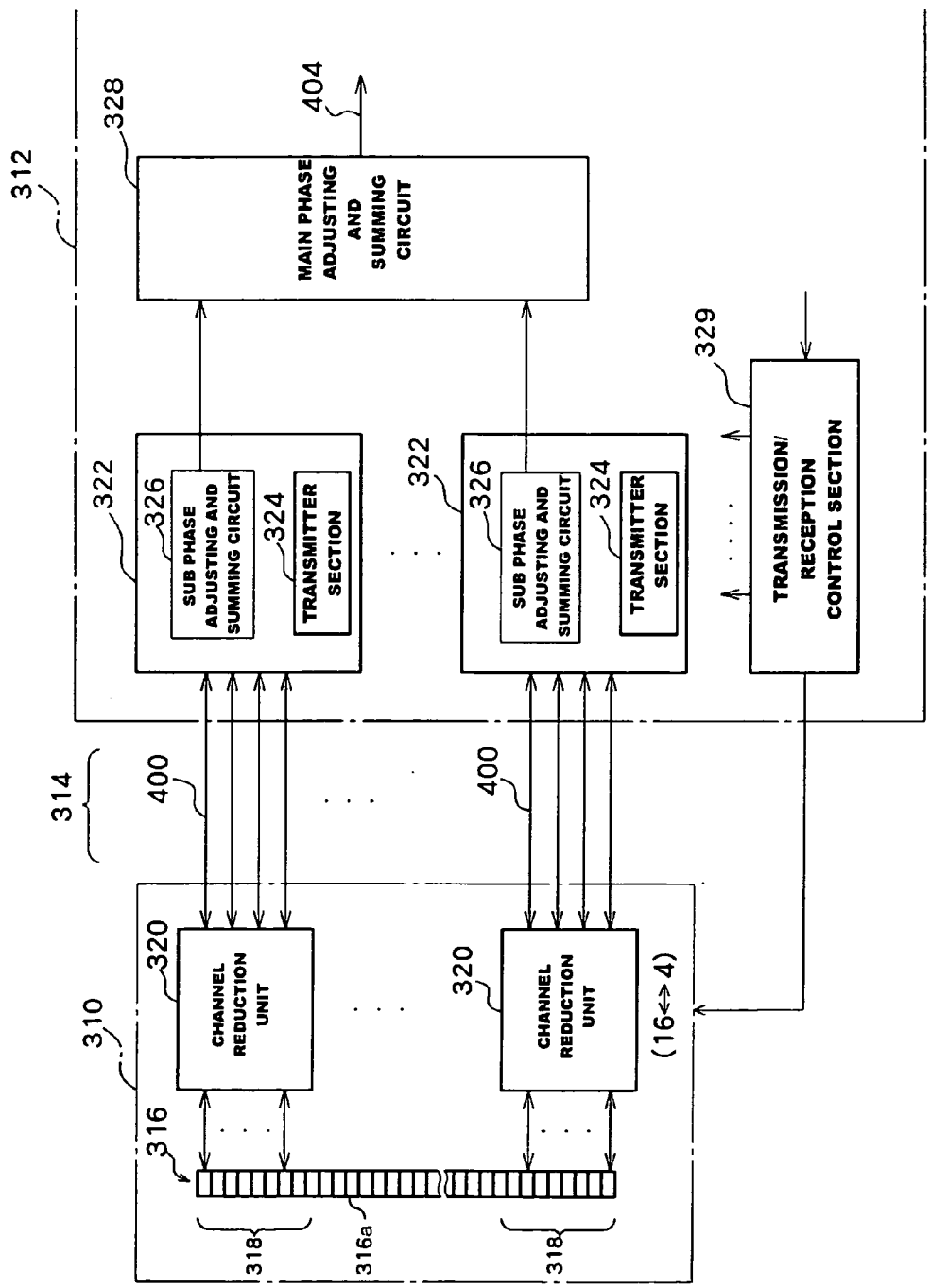
FIG. 12 is a block diagram showing a third embodiment of an ultrasound diagnosis apparatus of the present invention.

As described above, in the present embodiment, 16 FIFO memories 28, which are disposed in parallel with each other, are provided for each sub array 18. In the subsequent stage of these FIFO memories 28, 16 adders 30 are disposed in parallel with each other. Each adder 30 adds 16 signals output from the corresponding 16 specific FIFO memories 28 and outputs a receiving signal which has been phase-adjusted and summed (a main phase-adjusted and summed signal) 104. In other words, in the present embodiment, 16 main digital beam formers (main phase adjusting and summing circuits) 27 are provided within the apparatus body 12. Here, a beam forming technology is not limited to the digital beam forming as described in FIG. 1, and analog beam forming may also be applied. According to the present embodiment, sub phase adjusting and summing is performed within the probe head 10, and main phase adjusting and summing is performed within the apparatus body 12. With the above phase adjusting and summing processes performed in two stages, a receiving beam is finally formed. The electronic circuit such as a sub phase adjusting and summing circuit may also be provided within the probe connecter (not shown), as will be described below with regard to a second embodiment (FIG. 11). Further, the electronic circuit such as a sub phase adjusting and summing circuit may also be provided within the apparatus body, as will be described below with regard to a third embodiment (FIG. 12).

The transmission/reception control section 32 within the apparatus body 12 operates in accordance with a control signal 106 supplied from a main control section (not shown) to control the operation of each element shown in FIG. 1. More specifically, within the apparatus body 12, the transmission/reception control section 32 performs writing control and reading control with respect to a plurality of FIFO memories 28 and thereby achieves dynamic focus in receiving. Further, the transmission/reception control section 32 supplies a control signal to the probe head 10 through the control line 102. In accordance with the control signal, the sub transmission control section 22 and the sub reception control section 24 control the operation of a plurality of sub transmitter/receiver sections 20 within the probe head 10. The control signal is also used to select patterns in the grouping process which is performed by a multiplexer as will be described below with reference to FIG. 2. It should be noted that an electric power line and a clock signal supplied from the apparatus body 12 to the probe head 10 are not shown in FIG. 1.

FIG. 2 particularly shows a specific structure of a certain sub transmitter/receiver section 20 in the structure shown in FIG. 1. The plurality of sub transmitter/receiver sections 20 in FIG. 1 have the same structure. As described above, in the present embodiment, one sub array 18 is formed by 16 transducer elements 16a. One multiplexer 38 is provided corresponding to one sub array 18. The multiplexer 38 is a switching matrix serving as a switching means, and has the grouping function as described above. The multiplexer 38 performs a connecting process between 16 terminals arranged on the side of the array transducer 16 (namely, 16 element signal lines) and 4 terminals arranged on the side of the sub transmitter/receiver section 20 (namely, 4 group signal lines). With the multiplexer 38, a variety of group setting patterns (grouping patterns) can be established on the sub array 18, as will be described below with reference to FIGS. 4 to 6. In FIG. 2, numeral 102C indicates a control signal supplied from the apparatus body to the multiplexer 38 for selecting the switching pattern. Alternatively, a plurality of multiplexers may be formed by a single switching matrix circuit. The multiplexer 38 further includes a plurality of switches (not shown) provided respectively at intersections between the 16 element signal lines and the 4 group signal lines. With the ON/OFF operation of each of these switches, one or a plurality of element signal lines are connected to each group signal line.

The sub transmitter/receiver section 20 of the present embodiment includes 4 two-way transmission circuits (I/F circuits or input/output circuits) 42 used for signal transmission, a sub phase adjusting and summing circuit 34, and a transmitter section 36. In the present embodiment, each two-way transmission circuit 42 functions as a pulser/head amp circuit. Specifically, each two-way transmission circuit 42 supplies a transmitting signal supplied from the transmitter section 36 to the multiplexer 38 and, on the other hand, outputs a receiving signal output from the multiplexer 38 to the sub phase adjusting and summing circuit 34. In this case, it is preferable to transmit a receiving signal between the sub array 18 and the 4 two-way transmission circuits 42 in a current mode, and to transmit a transmitting signal between the sub array 18 and the 4 two-way transmission circuits 42 in a voltage mode.

The transmitter section 36 includes 4 memories (FIFO memories in this example) 56 and 4 D/A converters 48. Each FIFO memory 56 functions as a wave form generator, and the operation (the output timing, in particular) of the FIFO memory 56 is controlled by the sub transmission control section 22. Specifically, each FIFO memory 56 generates a transmitting signal waveform as a digital signal. A transmitting signal, which is a digital signal, output from each FIFO memory 56 is input to a D/A converter 48, where the input digital signal is converted into an analog signal. The transmitting signal, which is now an analog signal, is transmitted to the multiplexer 38 via the two-way transmission circuit 42 described above. The multiplexer 38 then determines one or a plurality of transducer elements forming the specific group corresponding to the transmitting signal as a destination of the signal. In this manner, 4 transmitting signals generated by the transmitter section 36 are individually supplied to the corresponding one of four groups forming a specific sub array 18.

The sub phase adjusting and summing circuit 34 includes 4 A/D converters 46, 4 memories (FIFO memories in this example) 50, an adder 52, and a D/A converter 54. Each A/D converter 46 converts an input receiving signal (a group receiving signal), which is an analog signal, into a digital signal. The receiving signal which is now converted into a digital signal is temporarily stored in the corresponding FIFO memory 50 and is read out and supplied to the adder 52 at suitable timing for phase adjusting. The adder 52 sums the 4 input receiving signals. The sub phase adjusting and summing process is thus completed. The sub phase adjusted and summed signal (digital signal) obtained by this adding process is then converted into an analog signal in the D/A converter 54. The sub phase-adjusted and summed signal which is now an analog signal is output to the signal line 100.

As described above, the sub phase adjusting and summing circuit 34 performs a phase adjusting and summing operation in the first stage, namely a sub phase adjusting and summing operation, and therefore corresponds to a sub digital beam former. The reading control, for example, with respect to the 4 receiving signals is performed by the sub reception control section 24. A control signal 102B for reception control is input to the sub reception control section 24 and a control signal 102A for transmission control is input to the sub transmission control section 22.

The structure of the transmitter section 36 which is illustrated in FIG. 2 is merely one example, and the transmitter section 36 may be constituted by an analog circuit, for example. In either case, delay time is set for each transmitting signal such that a transmitting beam is formed in the 2D array transducer 16 using a trigger signal supplied from the apparatus body side as a reference.

For example, it is possible to output a transmitting signal with a desired delay amount in synchronization with a trigger pulse, by appropriately setting the leading end of the storing position for the transmitting signal in the FIFO memory 56 and the data transfer timing of the transmitting signal. Further, the sub reception control section 24 may be formed as a delay data memory.

Figure 3:
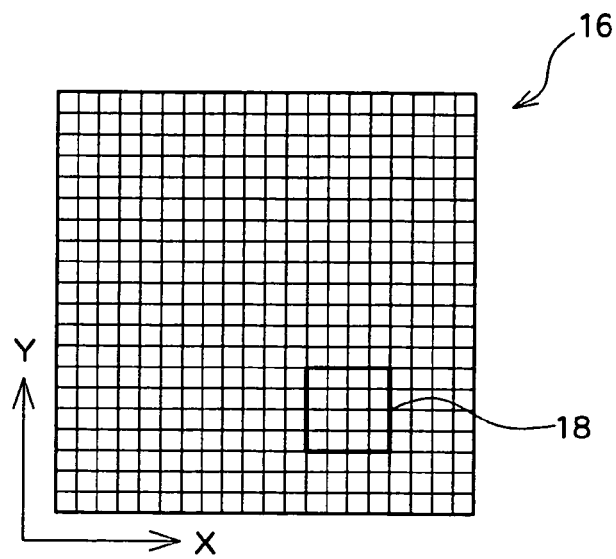
FIG. 3 is a view showing a relationship between an array transducer and a sub array.

FIG. 3 shows the array transducer 16. The array transducer 16 is a 2D array transducer having 50 transducer elements in the X direction and 50 transducer elements in the Y direction, for example. As described above, a plurality of sub arrays are defined with respect to the array transducer. More specifically, each of the plurality of sub arrays has a rectangular (square) shape and they are closely defined with no gap between each other over the whole region of the array transducer 16. FIG. 3 shows a representative one of these sub arrays 18. As described above, a plurality of groups are set for each sub array. A transmitting delay amount and a sub receiving delay amount in accordance with the focus and beam steering is provided to each group. Here, a main receiving delay amount is provided for each sub array. In other words, a common main receiving delay amount is provided to all the plurality of transducer elements forming each sub array. Accordingly, the total delay amount obtained by adding the sub receiving delay amount and the main receiving delay amount is provided to the individual transducer elements.

Figure 4:
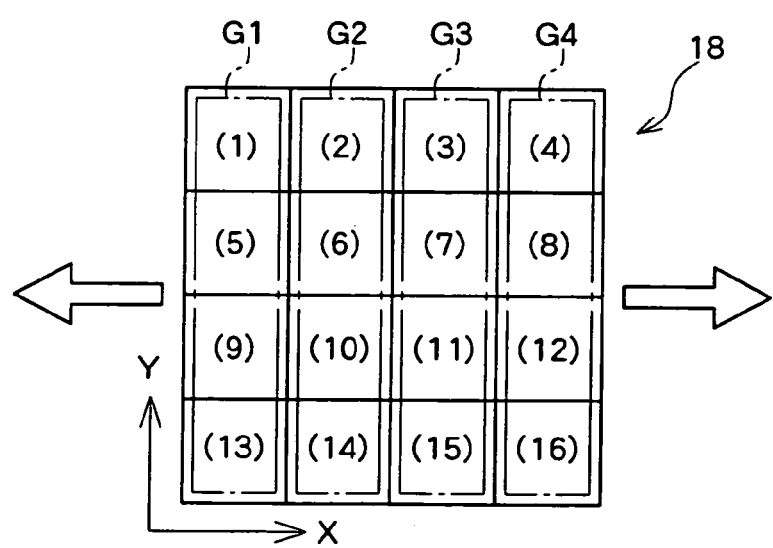
FIG. 4 shows a first example of grouping pattern on the sub array.
Figure 5:
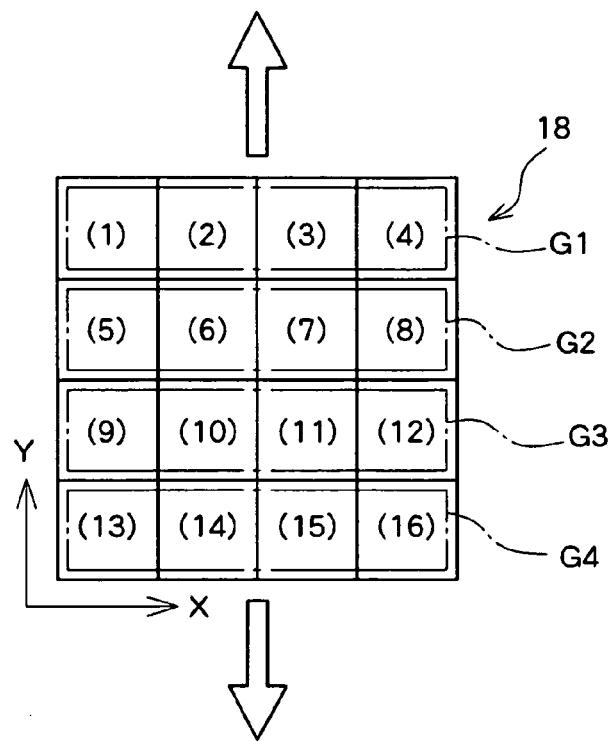
FIG. 5 shows a second example of grouping pattern on the sub array.
Figure 6:
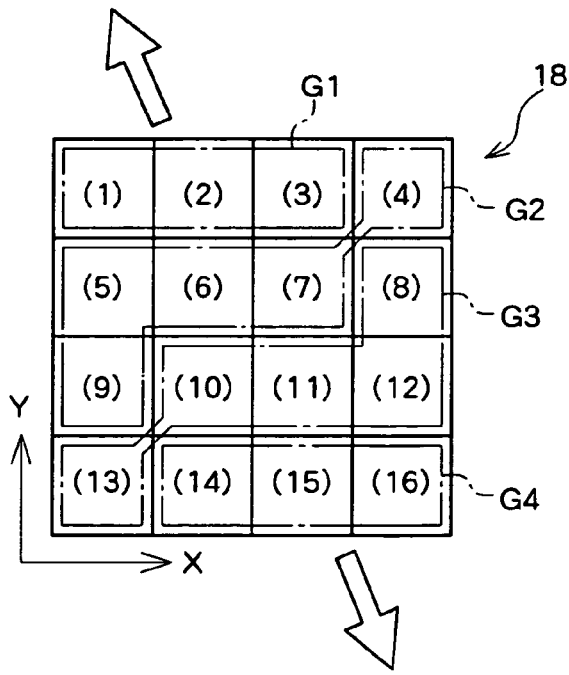
FIG. 6 shows a third example of grouping pattern on the sub array.

FIGS. 4 to 6 show examples of group setting patterns for the sub array. In the present embodiment, the same grouping pattern is established for a plurality of sub arrays. However, different grouping patterns may be set for all or part of the sub arrays at the time of each transmission.

In the example shown in FIG. 4, the beam scanning direction (beam deflecting (steering) direction) corresponds to the X direction. Four groups G1 to G 4 are defined side by side along the X direction. Each of the group G1 to G4 is formed by 4 transducer elements arranged in a line along the Y direction. In the example shown in FIG. 5, the beam scanning direction corresponds to the Y direction. Four groups G1 to G 4 are defined side by side along the Y direction. Each of the group G1 to G4 is formed by 4 transducer elements arranged in a line along the X direction. In the example shown in FIG. 6, the beam scanning direction is set in the diagonal direction crossing the X and Y directions. In this case, although 4 groups G1 to G4 are set, each group has a form (shape and number of elements) which differs from any of those shown in FIGS. 4 and 5. Specifically, the group G1 is composed of 3 transducer elements arranged along the X direction, and the group G2 is composed of 4 transducer elements arranged in an L shape form and 1 transducer element located at the upper right corner of the sub array 18. The group G3 has the same shape as the group G2, but their directions are different by 180 degree. The group G4 is composed of 3 transducer elements arranged along the X direction similar to the group G1, though the group G4 is set at the lower right corner of the sub array 18 while the group G1 is set at the upper left corner of the sub array 18. According to the present embodiment, the number of transducer elements forming each group can be variably (non-fixedly) set in accordance with the beam scanning direction, as shown in FIGS. 4 to 6.

When determining the form of each group, it is desirable to reduce side lobe to the greatest possible extent. By setting a larger number of groups per sub array, the degree of freedom for grouping patterns increases and more preferable beam can be formed accordingly. In this case, however, the advantage of channel reduction is reduced. It is therefore desirable to determine the number of transducer elements and the number of groups forming one sub array in accordance with the accuracy required for beam profile.

As described above, according to the present embodiment, it is possible to freely set the number of transducer elements forming each group. In the example shown in FIG. 6, in order to obtain a preferable beam profile in accordance with the beam scanning direction, each of the groups G1 and G4 is composed of 3 transducer elements and each of the groups G2 and G3 is composed of 5 transducer elements. It is desirable to dynamically change the grouping pattern in this manner in accordance with the beam scanning direction. This will be further described in detail with reference to FIGS. 19 and 20.

Figure 19:
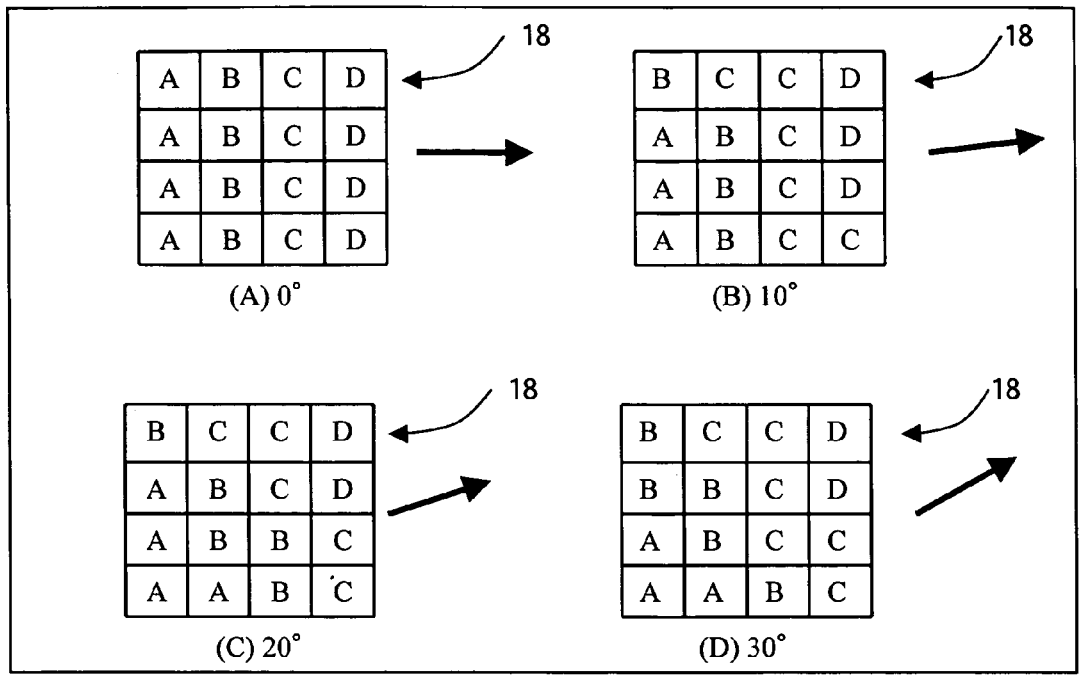
FIG. 19 shows another example of grouping pattern on the sub array.

FIG. 19 shows one example in which the grouping pattern changes with a change in beam scanning direction. In the example shown in FIG. 19, all the transducer elements forming the sub array 18 function as effective transducer elements. FIG. 19(A) shows a grouping pattern when the beam scanning direction is 0 degree (which is the same as the pattern shown in FIG. 4), FIG. 19(B) shows a grouping pattern when the beam scanning direction is 10 degree, FIG. 19(C) shows a grouping pattern when the beam scanning direction is 20 degree, and FIG. 19(D) shows a grouping pattern when the beam scanning direction is 30 degree. As shown, the shape of each group and the number of transducer elements forming each group vary in accordance with the beam scanning direction, so that a preferable beam profile can be formed.

Figure 20:
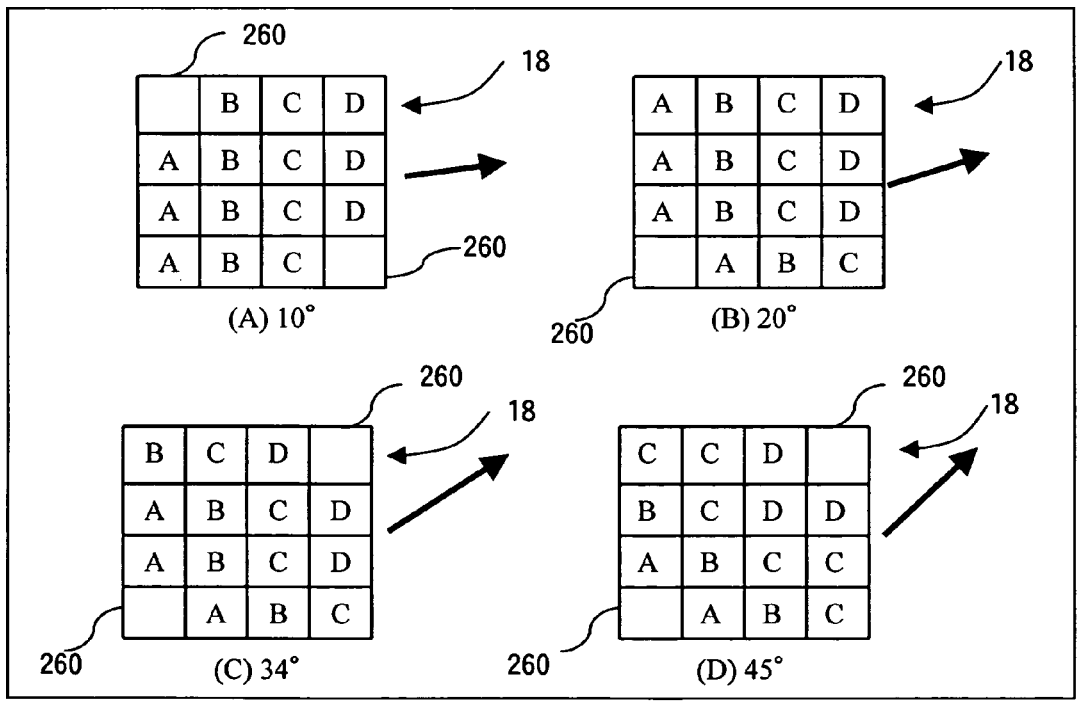
FIG. 20 shows still another example of grouping pattern on the sub array.

FIG. 20 shows another example in which the grouping pattern changes with a change in beam scanning direction. In the example shown in FIG. 20, a portion of all the transducer elements forming the sub array 18 are ineffective transducer elements 260, and the remaining transducer elements are effective transducer elements. FIG. 19(A) shows a grouping pattern when the beam scanning direction is 10 degree, FIG. 19(B) shows a grouping pattern when the beam scanning direction is 20 degree, FIG. 19(C) shows a grouping pattern when the beam scanning direction is 34 degree, and FIG. 19(D) shows a grouping pattern when the beam scanning direction is 45 degree. As shown, the shape of each group and the number of transducer elements forming each group vary in accordance with the beam scanning direction, and the number of ineffective transducer elements also varies, so that a preferable beam profile can be formed.

Figure 7:
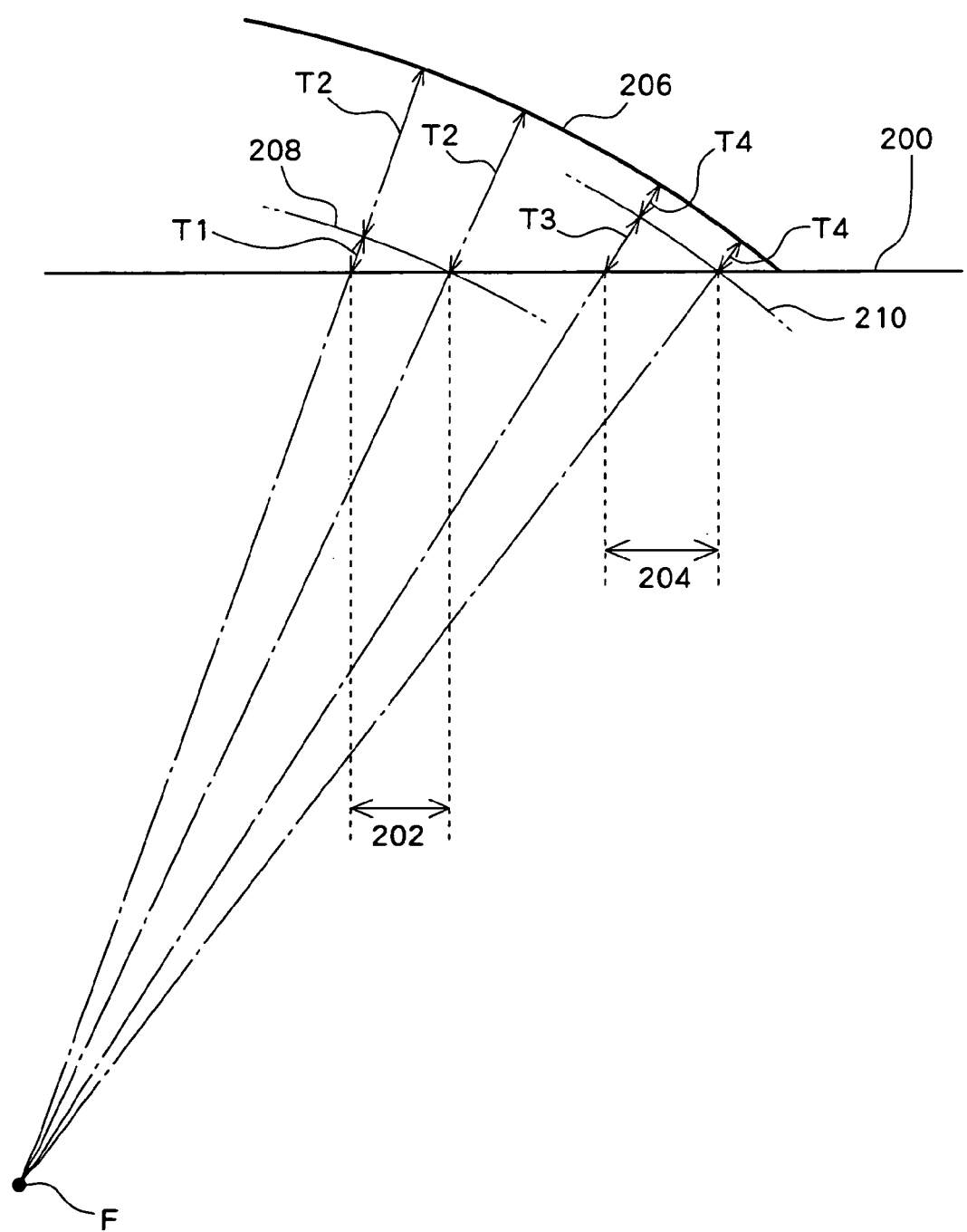
FIG. 7 is a view for explaining a relationship between a main delay (main delay amount) and sub delay (sub delay amount)

FIG. 7 conceptually shows a relationship between the sub delay amount in the sub phase adjusting and summing process and the main delay amount in the main phase adjusting and summing process. The sub delay amount is a relative delay amount which is determined for each group, and the main delay amount corresponds to an offset delay amount with respect to each sub array as a whole. In the present embodiment, the receiving delay amount for each group can be divided into the sub delay amount and the main delay amount corresponding to the two-stage phase adjusting and summing process. On the other hand, the transmitting delay amount for each group cannot be divided in that manner.

Referring to FIG. 7, numeral 206 indicates a line having an equal distance from a focus F, and such a line 206 can be regarded as a virtual sound source having a scope. If the transducer elements are arranged on this line 206, phases of the ultrasound transmitted from the transducer elements can be completely matched on the focus F, and phases of ultrasound (reflected waves) received by the transducer elements can also be matched completely. In actual practice, however, a plurality of transducer elements are arranged on an actual transducer plane indicated by numeral 200, and the focus F may move. Known electronic focusing technologies are therefore applied so as to match the phases of ultrasound transmitted from each transducer element with respect to the focus F and also match the phases of receiving signals output from the transducer elements. In the present embodiment, an electronic delay process with respect to a transmitting signal and a receiving signal is performed for each group in each sub array.

Referring to FIG. 7, numerals 202 and 204 indicate a partial opening corresponding to a sub array. According to the geometrical relationship shown in FIG. 7, the largest delay time is given to the left end portion (a group on the left end side) of the partial openings 202 and 204, and the smallest delay time is given to the right end portion (a group on the right end side) of the partial openings 202 and 204. Lines 208 and 210 are drawn at equal distances from the focus F, respectively, and pass through the right ends of the partial openings 202 and 204, respectively in the example shown in FIG. 7. With respect to the partial opening 202, the distance between the line 208 and the line 206 corresponds to the main delay amount, which is indicated by T2. Further, on the left end of the partial opening 202, the sub delay amount T1 is shown between the actual transducer plane 200 and the line 208. In other words, the main delay amount is common over the whole of the partial opening 202, whereas the sub delay amount is different depending on the group position (e.g., the center position of the group) within the partial opening 202. Similarly, with respect to the partial opening 204, the main delay amount is represented by T4 and the sub delay amount on the left end is represented by T3. While the sub delay time is individually determined for each group in each sub array in the present embodiment, it is also possible to set the same sub delay time with respect to the transducer elements having the same element number (the same element position or the same element address) for a plurality of sub arrays. With such a structure, although beam focusing property is lowered, control can be simplified.

Figure 8:
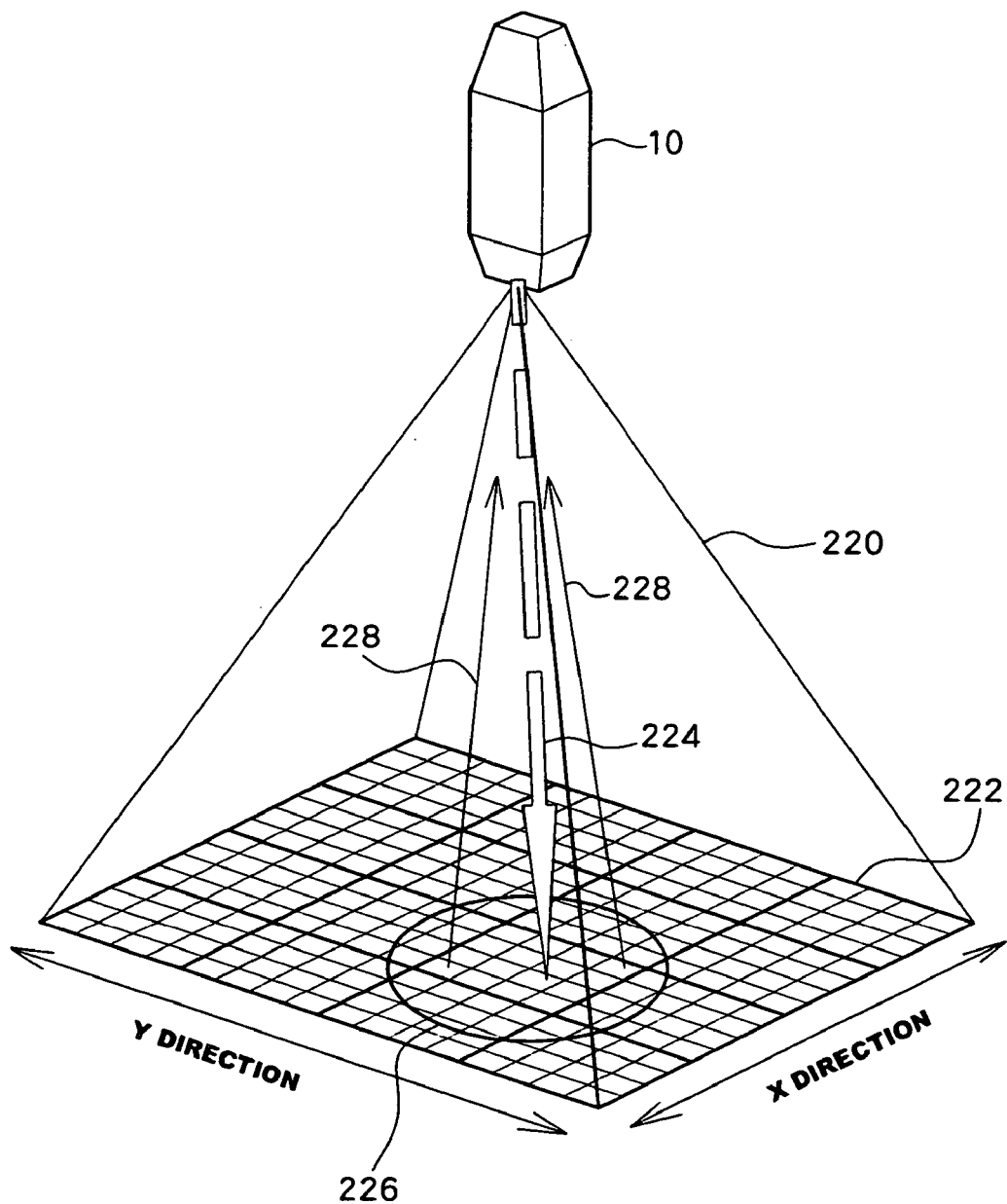
FIG. 8 is a view showing a state in which 16 receiving beams are simultaneously formed with respect to one transmitting beam.

FIG. 8 shows a relationship between the probe head 10 and a part of the three-dimensional echo data acquiring space. Numeral 224 indicates a transmitting beam. In the present embodiment, 16 receiving beams 228 are simultaneously formed with respect to one transmitting beam 224.

A matrix 222 which is schematically shown as a bottom surface of the three-dimensional echo data acquiring space 220 represents addresses of the receiving beam 228. In the FIG. 8, 16 addresses are shown in the X direction and 16 addresses are shown in the Y direction, which results in total of 256 addresses for the receiving beam. As conceptually shown by a circle indicated by numeral 226, the transmitting beam 224 has a broad beam profile covering 16 receiving beams 228. On the other hand, each receiving beam 228 has a sharp beam profile.

Figure 10:
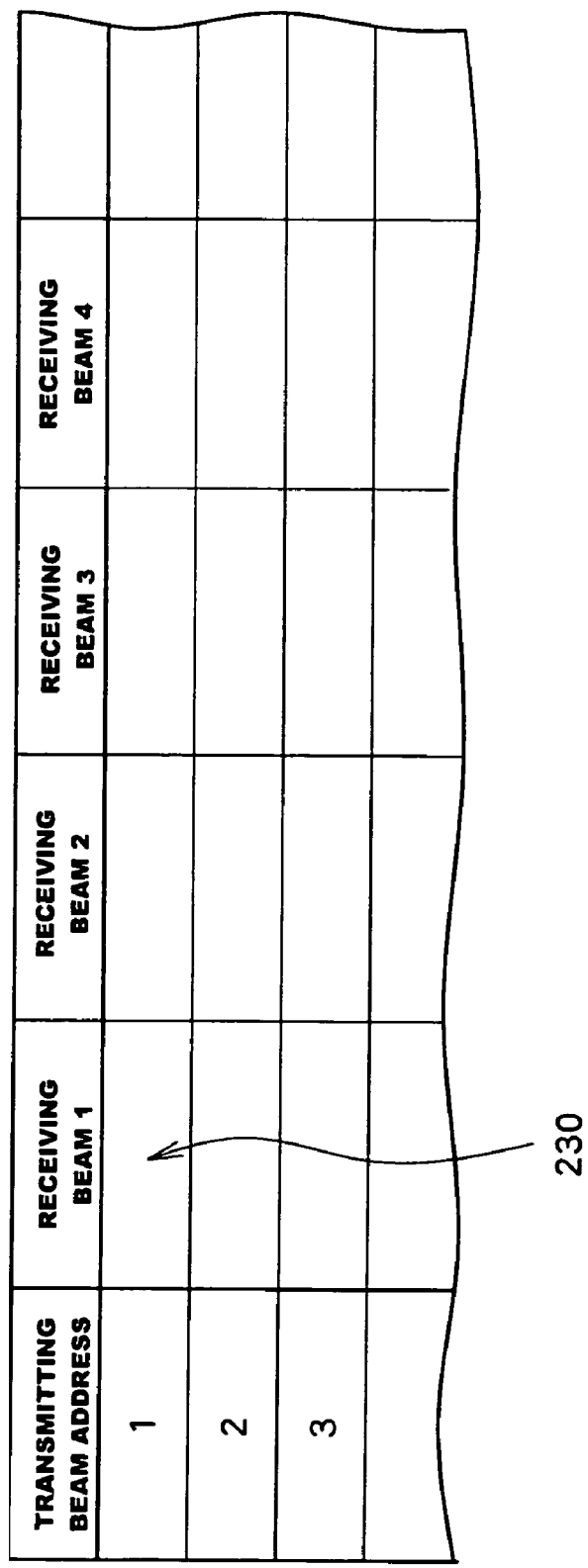
FIG. 10 is a view showing a relationship between the transmitting beam address and a set of main delay amounts for each receiving beam.

FIGS. 9 and 10 show tables indicating transmitting and receiving conditions. As shown in FIG. 9, when the transmitting beam address is set, the grouping pattern, a set of transmitting delay amounts, and a set of receiving sub delay amounts (see numeral 229) are determined for each sub array. The set of transmitting delay amounts, in this example, is composed of four delay amounts given to four groups forming a sub array. The set of receiving sub delay amounts is composed, in this example, of four sub delay amounts given to four groups forming a sub array. Here, the value of each sub delay amount forming the set of receiving sub delay amounts may be dynamically varied in accordance with the depth of a receiving point.

FIG. 10 shows a set of receiving main delay amounts 230 for each receiving beam which is set for each transmitting beam address. In the present embodiment, the receiving main delay amount set 230 is composed of 128 main delay amounts, and each main delay amount is dynamically variable in accordance with the depth of a receiving point so as to achieve dynamic focus in receiving.

Here, it is also possible that the transmitter section 36 shown in FIG. 2 generates a low voltage transmitting signal for each group. In this case, the voltage of a transmitting signal is approximately between several volt and ten-odd volt, such as ±4.5V and ±9V. When a layered type transducer element, for example, is used as the transducer element 16a, it is possible to reduce the electrical impedance thereof to approximately several hundred ohms. When such a transducer element 16a is used, it is possible to obtain sufficient acoustic power even when the transducer element 16a is driven with a low voltage. However, the transducer elements may be driven with a high voltage as in the conventional manner.

With the above-described embodiment, because grouping and sub phase adjusting and summing is performed within the probe head 10, whereby 16 receiving signals are combined into one sub phase-adjusted and summed signal, the advantage of remarkably reducing the number of signal lines forming the probe cable 14 can be achieved. Further, because the transmitter section is provided within the probe head 10, the necessity of supplying a transmitting signal from the apparatus body 12 side for each transmission channel, namely for each group, can be eliminated, and the apparatus body 12 need only to remotely control the transmitter section within the probe head 12. In addition, according to the present embodiment, because 16 receiving beams are simultaneously formed for one transmitting beam, namely because 16 pieces of receiving information can be obtained in one transmitting/receiving process, the advantage of increasing the volume rate can be achieved. By using a plurality of receiving signals which have been subjected to the main phase adjusting and summing process thus obtained, a three-dimensional ultrasonic image, or a tomography image corresponding to a cross section when the three-dimensional data acquiring space is observed from an arbitrary direction, is formed.

While a sub phase adjusted and summed signal is transmitted in the form of an analog signal between the probe head 10 and the apparatus body 12 in the present embodiment, it is of course possible to transmit a sub phase adjusted and summed signal in the form of a digital signal.

Next, second and third embodiments will be described with reference to FIGS. 11 to 17. In the second and third embodiments, similar to the first embodiment described above, a multiplexer is used for performing grouping (channel reduction) within the probe head. The sub phase adjusting and summing process is, however, performed within the connector (FIG. 11) or the apparatus body (FIG. 12), not within the probe head. In the second and third embodiments, similar to the first embodiment, various grouping patterns including the grouping patterns shown in FIGS. 4, 5, 6, 19, and 20 can be established.

FIG. 11 shows the second embodiment of the present invention. An ultrasound diagnosis apparatus is roughly formed by a probe unit and an apparatus body 312. The probe unit is composed of a probe head 310, a probe cable 314A, and a cable connector 314B. The probe cable 314A includes a plurality of signal lines which will be described below. The cable connector 314B, which has a box shape, is detachably connected to the apparatus body 312. In the example shown in FIG. 11, an electronic circuit which will be described below is contained within the cable connector 314B. However, the electronic circuit may be provided within the apparatus body, as will be described with reference to FIG. 12.

The probe head 310 is used in contact with a surface of a living body, for example, for performing transmission and reception of ultrasound. The probe head 310 includes a 2D array transducer 316 which is composed of a great number of (about 4000, for example) transducer elements 316a. An ultrasonic beam is formed by the 2D array transducer 316 and is electronically scanned in a two-dimensional manner.

A plurality of 2D sub arrays 318 are defined with respect to the 2D array transducer 316 (see FIG. 3). In the present embodiment, 128 sub arrays are defined. In the present embodiment, each sub array is composed of 16 transducer elements 316a. The plurality of sub arrays 318 are closely coupled with each other on the 2D array transducer 316. Each sub array 318 has a rectangular shape and is defined fixedly. It is also possible, however, to adaptively vary the form of each sub array in accordance with the transmission/reception conditions (particularly the beam scanning direction), for example.

In the present embodiment, 128 channel reduction units 320 are provided corresponding to 128 sub arrays 318. In other words, one sub array 318 corresponds to one channel reduction unit 320. Each channel reduction unit 320 has a function of grouping 16 transducer elements forming a specific sub array corresponding thereto into 4 groups. With this function, the channel reduction ratio of 1/4 is achieved. When attention is focused on a certain sub array 318, 4 transmitting signals supplied from the apparatus body 12 side are supplied to the four groups, respectively. Because one group is normally composed of two or more transducer elements, one transmitting signal is supplied to two or more transducer elements in parallel. With respect to receiving, 16 receiving signals are combined into 4 group receiving signals. Because one group is normally composed of two or more transducer elements, two or more receiving signals are summed to generate one group receiving signal. As will be described below, in this embodiment, such a summing process of a plurality of receiving signals can be achieved by connecting a plurality of signal lines in the multiplexer. In this case, a plurality of receiving signals may be subjected to weighted addition.

In any case, because 16 transducer elements are grouped into four groups for each sub array 318, there is an advantage that both the number of transmitting channels and the number of receiving channels can be reduced to one fourth, within the probe head 310. Further, as will be described below, because a plurality of transmitter sections 324 are provided outside the probe head 310, problems such as an increased power consumption and increased physical scale resulting from providing a plurality of transmitter sections within the probe head 310 can be eliminated. More specifically, while a plurality of transmitter sections are provided within the probe head in the first embodiment described above, in the structure shown in FIG. 11, a plurality of transmitter sections 324 are provided within the connector 314B as will be described below.

The probe cable 314A includes a plurality of signal lines 400. Specifically, 4 signal lines 400 are provided for each sub array 318, and a total of 128×4 signal lines 400 are provided for the whole 2D array transducer 316. One or more control lines 402A are also included in the probe cable 314A separately from these signal lines 400. The control line 402A is used to control the operation of each element within the probe head 310. It should be noted that a power supply line supplied from the apparatus body 312 side to the probe head 310 or the like is not shown in FIG. 11.

In the structure example shown in FIG. 11, a plurality of transmission/reception modules 322 are provided within the cable connector 314B. One transmission/reception module 322 is provided for each sub array, and, in the present embodiment, a total of 128 transmission/reception modules 322 are provided within the cable connector 314B.

Each transmission/reception module 322 includes the transmitter section 324 and a sub phase adjusting and summing circuit 326. As will be described below, the transmitter section 324 includes 4 transmitters which output 4 transmitting signals, respectively. The 4 transmitting signals are supplied to the corresponding channel reduction unit 320 via the probe cable, and then supplied to the 4 groups, respectively.

The sub phase adjusting and summing circuit 326 performs, as a phase adjusting and summing process at the first stage, a sub phase adjusting and summing process with respect to the 4 group receiving signals which are input. As a result, these 4 receiving signals are combined into one sub phase adjusted and summed signal, which is indicated by numeral 403. A main phase adjusting and summing circuit 328 and a transmission/reception control section 329 are provided within the apparatus body 312. The main phase adjusting and summing circuit 328 performs a main phase adjusting and summing process with respect to 128 phase adjusted and summed signals obtained corresponding to the 128 sub arrays. In other words, the main phase adjusting and summing circuit 328 performs a phase adjusting and summing process at the second stage, thereby obtaining a main phase adjusted and summed signal 404. As described above, the phase adjusting and summing means is composed of a plurality of sub beam formers and a single main beam former. The receiving signals are transmitted between the cable connector 314B and the apparatus body 312 basically using 128 transmission lines. This provides an advantage that the signal transmitting method for existing ultrasound diagnosis apparatuses can be used as it is. There is another advantage that a beam former provided in an existing ultrasonic diagnosis apparatus can be used as the main phase adjusting and summing circuit 328. Alternatively, it is, of course, possible to provide a dedicated main phase adjusting and summing circuit 328.

The operation of the transmission/reception control section 329 is controlled by a main control section (not shown), to thereby control the operation of each element shown in FIG. 11. In particular, the transmission/reception control section 329 outputs a control signal 402B to each element within the probe connector 314B and outputs a control signal 402A to each element within the probe head 310.

While a single main phase adjusting and summing circuit 328 is provided within the apparatus body 312 in the embodiment shown in FIG. 11, any desired number of main phase adjusting and summing circuits 328 may be provided in parallel, similar to the first embodiment described above, to simultaneously form a plurality of receiving beams in one transmitting process.

FIG. 12 shows a third embodiment of the present invention, in which elements similar to those in FIG. 11 are designated by similar numerals and therefore will not be described again. In the structure example shown in FIG. 12, the plurality of transmission/reception modules 322 shown in FIG. 11 are provided within the apparatus body 312. The probe connector is omitted in FIG. 12. This structure can similarly provide an advantage of reducing the number of signal lines 400 by means of channel reduction performed within the probe head 310. The transmission/reception control section 329 controls the operation of each element shown in FIG. 12, and supplies a control signal to the probe head 310.

In the structures shown in FIGS. 11 and 12, with respect to signal transmission in the probe cable 314, a transmitting signal may be transmitted as a voltage signal and a receiving signal may be transmitted as a current signal. Further, the transmitting signal may be a low voltage signal in the range of several V to ten-odd V, for example, such as ±4.5V or ±9V. When such a low voltage transmitting signal is used to drive each transducer element, it is desirable to use a layered element as each transducer element, so that each transducer element will have electrically low impedance. With this structure, it is possible to obtain sufficient acoustic power even by driving with a low voltage. However, a signal of high voltage such as 100V, for example, may also be used as the transmitting signal.

In the third embodiment, similar to the first (and the second) embodiment, the array transducer 316 is formed as a 2D array transducer. A plurality of sub arrays 318 are defined on the array transducer 316 (see FIG. 3). Each sub array 318 has a rectangular shape. Also, in the third embodiment, similar to the first embodiment, grouping patterns are set in accordance with the transmission and reception conditions for each sub array 318 (see FIGS. 4 to 6). Further, in the third embodiment, similar to the first and second embodiments, a sub delay amount is set for each group, and a main delay amount is set for each sub array, in accordance with the conditions shown in FIG. 7.

The example structures of the channel reduction unit 320 and the transmission/reception module 322 in the second and third embodiments will be described, with reference to FIGS. 13 to 16. In these drawings, similar elements are designated by the same numerals.

Figure 13:
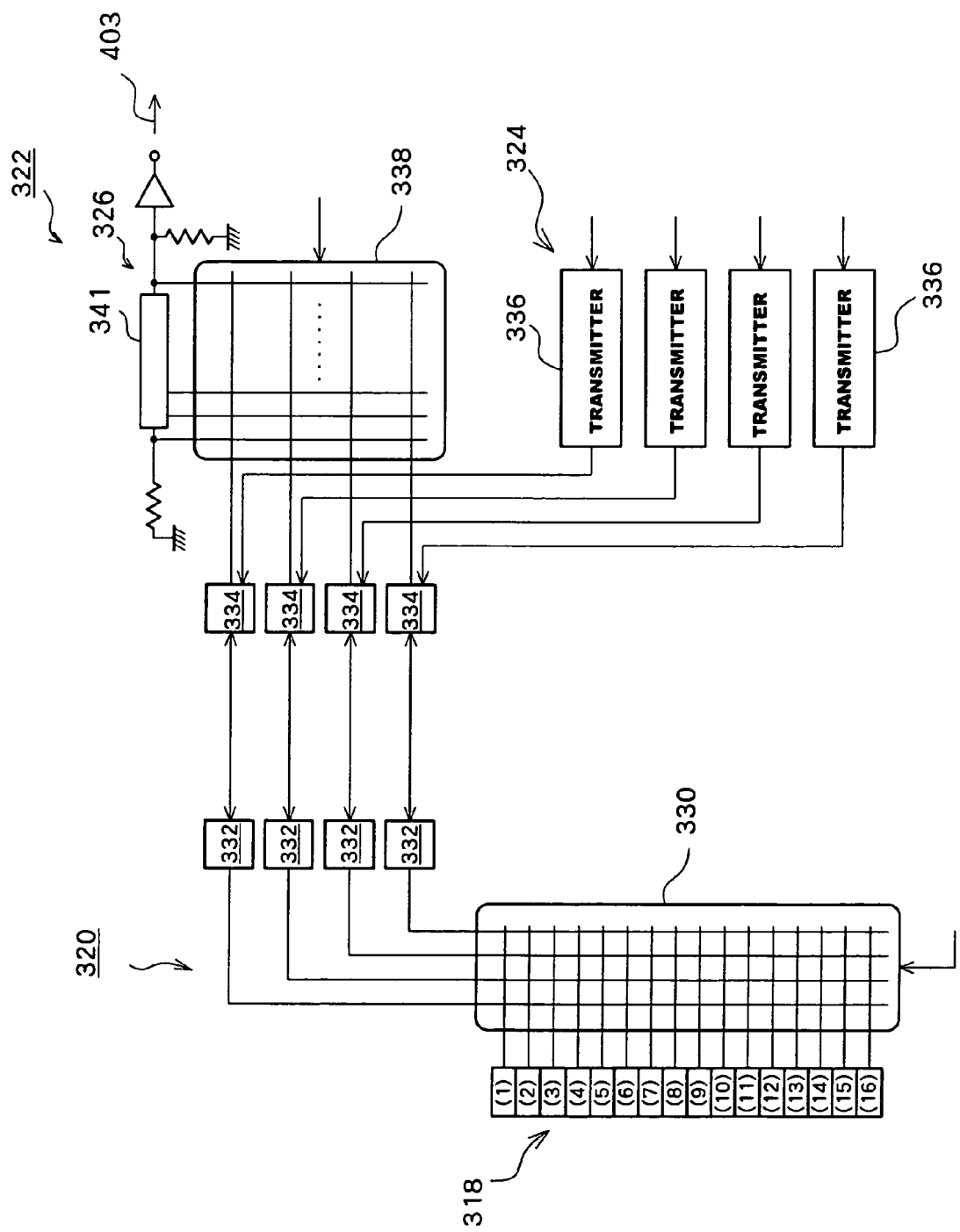
FIG. 13 is a first example structure of a channel reduction unit and a transmission/reception module.

Referring to FIG. 13, the multiplexer 330 is connected to the sub array 318. The multiplexer 330 is a switching matrix, and therefore functions as a switching means or a group setting means. The multiplexer 330 has 16 terminals on the side of the sub array 318 and 4 terminals on the side of the probe cable. Accordingly, any desired line connection can be achieved between these 16 terminals and 4 terminals, which allows the setting of desired grouping patterns. Although, similar to the previous embodiments, the number of transducer elements forming each group is variably set in the present embodiment, the number of transducer elements can be set the same for all of the groups. Further, the same grouping pattern may be used for a plurality of sub arrays, or a desired grouping pattern may be set for each sub array in accordance with the position of the sub array and the transmission/reception conditions.

In the example structure shown in FIG. 13, 4 two-way transmission circuits 332 are provided in the channel reduction unit 320. The two-way transmission circuit 332 has a function of transmitting a receiving signal and a transmitting signal, and operates as a current to voltage conversion circuit, for example. Various structures can be used for the two-way transmission circuit 332 and a two-way transmission circuit 334 which will be described below.

On the other hand, a plurality of transmitters 336 forming a transmitter section 324 are provided in the transmission/reception module 322. In the present embodiment, 4 transmitters 336 are provided and generate 4 transmitting signals. These transmitting signals are supplied to the probe head side via 4 transmission circuits 334, respectively, provided within the transmission/reception module 332. Each of the two-way transmission circuits 334 functions as a terminal circuit for accepting a receiving signal and also as a circuit for transmitting a transmitting signal.

The transmission/reception module 322 includes a sub phase adjusting and summing circuit 326 which functions as a sub beam former. In the example shown in FIG. 13, the sub phase adjusting and summing circuit 326 is formed as an analog phase adjusting and summing circuit. More specifically, the sub phase adjusting and summing circuit 326 includes a switching matrix 330 and a delay line 341. The delay line 341 has a great number of taps corresponding to respective delay amounts, and the switching matrix 330 supplies each of the 4 input receiving signals to a tap which corresponds to the receiving sub delay amount of the signal, whereby a sub phase adjusting and summing process is achieved in an analog manner. With the above process, a sub phase adjusted and summed signal 403 is generated. The switching matrix 330 includes a plurality of switches (not shown) provided respectively at intersections between 16 element signal lines and 4 group signal lines. With the ON/OFF operation of each of these switches, one or a plurality of element signal lines are connected to each group signal line.

Figure 14:
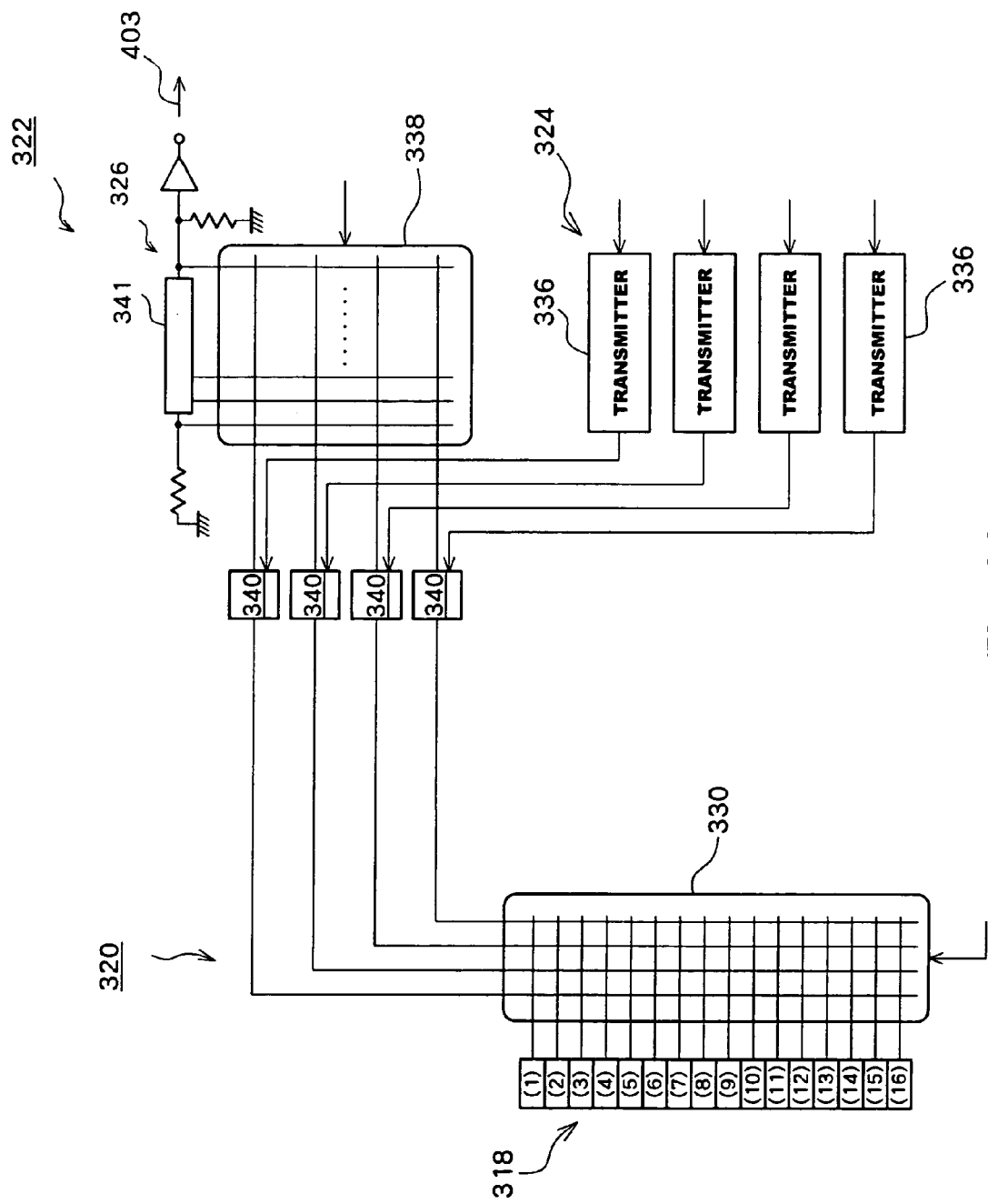
FIG. 14 is a second example structure of a channel reduction unit and a transmission/reception module.

In the structure example shown in FIG. 14, a plurality of two-way transmission circuits 340 are provided within a transmission/reception module 322. These transmission circuits 340 are directly connected to the multiplexer 330. Each transmission circuit 340 may function as a pulser used for transmission and a head amp circuit used for reception.

Figure 15:
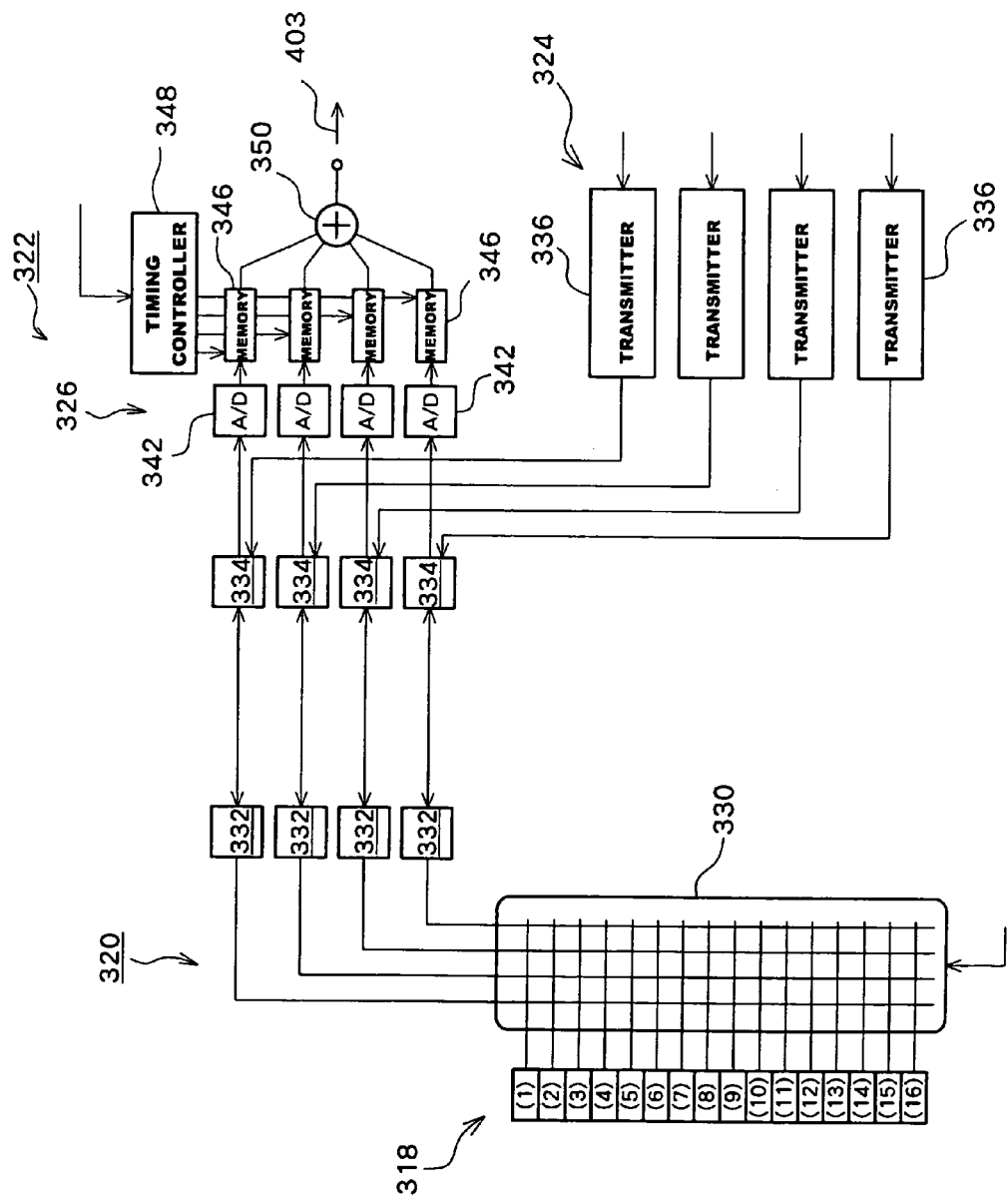
FIG. 15 is a third example structure of a channel reduction unit and a transmission/reception module.

In the structure example shown in FIG. 15, the sub phase adjusting and summing circuit 326 is formed in the form of a digital beam former. Specifically, the sub phase adjusting and summing circuit 326 includes 4 A/D converters 342, 4 memories 346, an adder 350, and a timing controller 348. A receiving signal (a group receiving signal) output from each transmission circuit 334 is supplied to the corresponding one of A/D converters 342, where the input analog signal is converted into a digital signal, which is then stored temporarily in the memory 346. The timing controller 348 controls the signal reading timing with respect to the 4 memories 346 to thereby assign delay time to each signal. The 4 signals thus read out from the 4 memories 346 are summed in the adder 350. As a result, a sub phase adjusted and summed signal 403 is obtained in the form of a digital signal.

Figure 16:
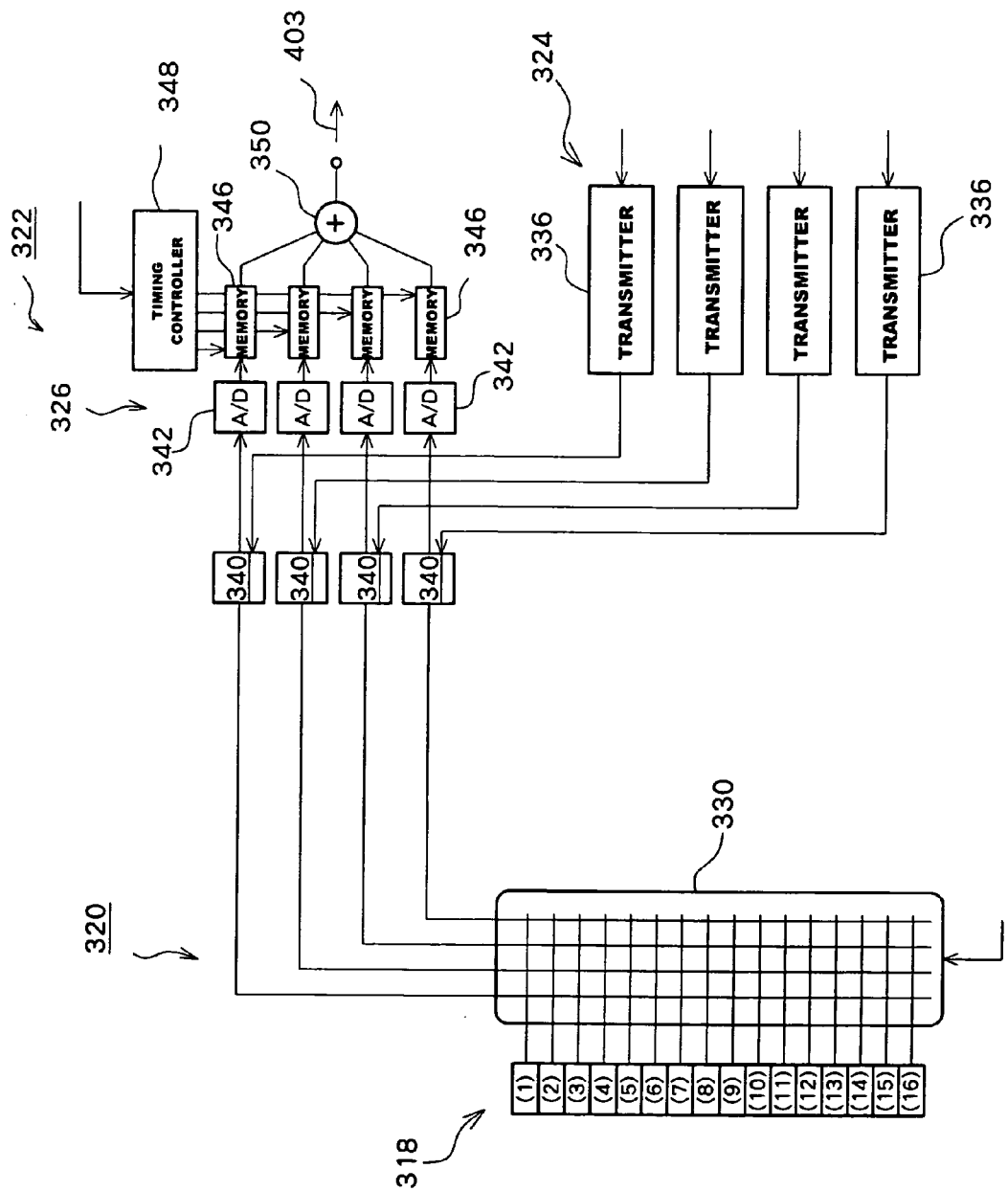
FIG. 16 is a fourth example structure of a channel reduction unit and a transmission/reception module.

The example structure shown in FIG. 16 is the same as the example structure shown in FIG. 15 in that the transmission/reception module 322 includes a sub digital beam former, and differs from the example structure of FIG. 15 in that 4 two-way transmission circuits 340 are provided only on the side of transmission/reception module 322. Specifically, each transmission circuit 340 functions as a pulser/head amp circuit similar to each transmission circuit 340 shown in FIG. 14, and is directly connected to the multiplexer 330.

Figure 17:
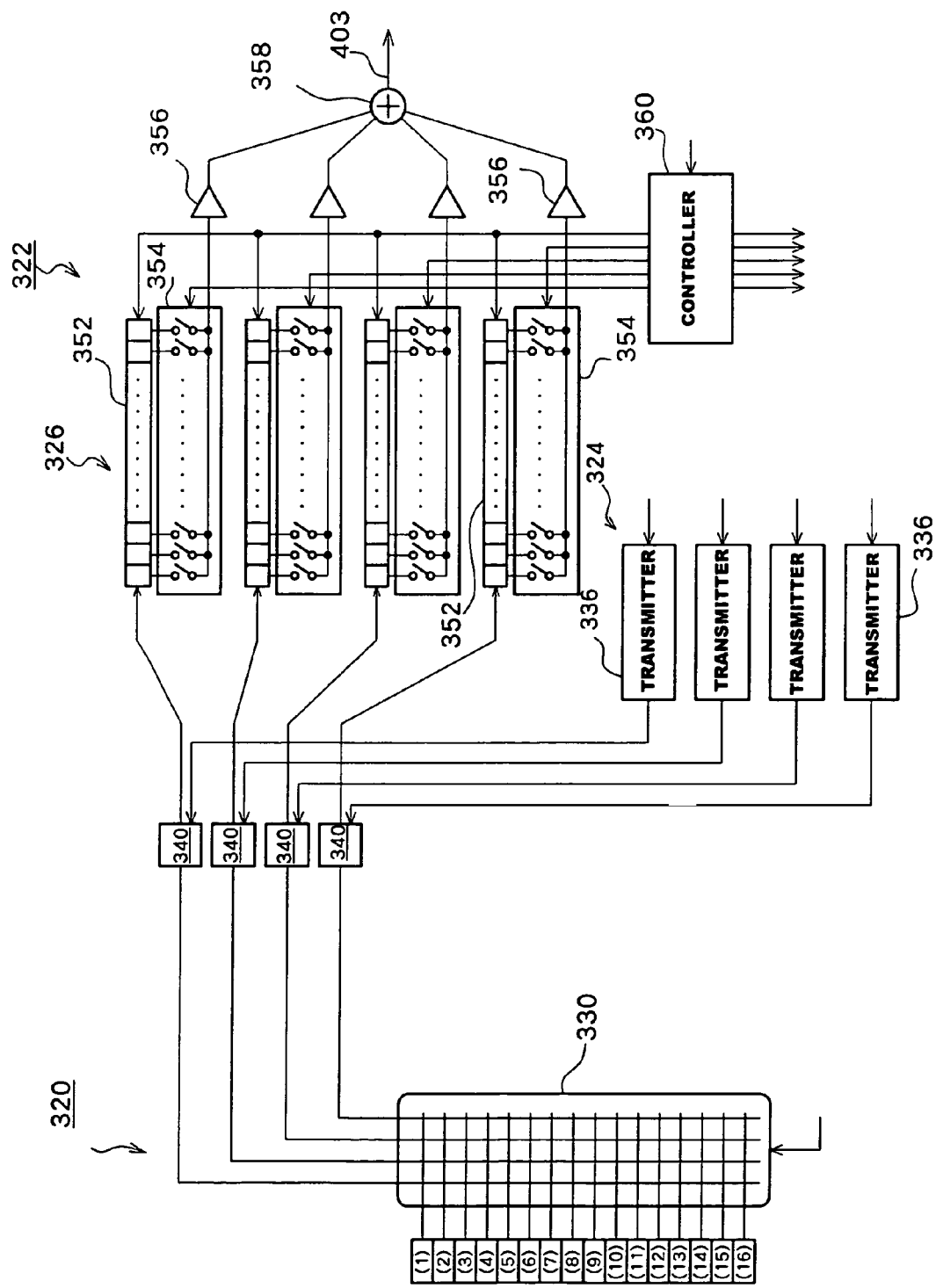
FIG. 17 is a fifth example structure of a channel reduction unit and a transmission/reception module.

In the example structure shown in FIG. 17, while the transmission/reception module 322 includes 4 transmission circuits 340 similar to the structure shown in FIG. 16 (and FIG. 14), the sub phase adjusting and summing circuit 326 is formed in the form of an analog phase adjusting and summing circuit which uses a CCD device. More specifically, 4 CCDs and 4 switching circuits 354 are provided corresponding to 4 receiving signals (4 group receiving signals), and the controller 360 supplies a clock signal to the CCDs 352 and supplies a control signal to the switching circuits 354.

In the CCDs 352, an input signal is sequentially transmitted in synchronization with a clock and is extracted from a position which is specified by the controller 360. In other words, by appropriately setting such a point for extracting a signal, desired delay time can be given to the signal. The extracted signal is output to the adder 358 via an amplifier 356. The 4 signals which have been subjected to the delay process are summed in the adder 358, so that a sub phase adjusted and summed signal 403 is generated in the form of an analog signal. The controller 360 controls a plurality of sub phase adjusting and summing circuits as a whole.

As described above, according to the first, second and third embodiments of the present invention, because 16 receiving signals, for example, are grouped into 4 groups, for example, for each sub array, namely because channel reduction is achieved within the probe cable, the number of signal lines for transmitting within the probe cable can be reduced. Further, in the above first, second, and third embodiments, because the grouping pattern of each sub array is dynamically changed in accordance with the transmission/reception conditions, preferable beams can be formed. In particular, the number of transducer elements forming each group can be varied, so that side lobes can be reduced or a preferable beam profile can be obtained.

What is claimed is:
1. An ultrasound diagnosis apparatus including a probe unit and an apparatus body to which the probe unit is detachably connected, the ultrasound diagnosis apparatus comprising:

a 2D array transducer composed of a plurality of transducer elements which are divided into a plurality of 2D sub arrays;

a group setting section for setting a plurality of groups with respect to a plurality of transducer elements within each sub array in accordance with a beam forming condition, the group setting section being capable of varying the number of transducer elements forming each of the groups;

a transmitter section for supplying a plurality of transmitting signals to the plurality of groups which are set with respect to each sub array;

a receiver section for processing a plurality of group receiving signals corresponding to the plurality of groups which are set with respect to each sub array; wherein the group setting section stuns a plurality of receiving signals for each group to perform receiving channel reduction at the time of receiving, and outputs an identical transmitting signal to a plurality of transducer elements for each group in parallel to perform transmitting channel reduction at the time of transmitting;

the receiver section includes:
a plurality of sub phase adjusting and summing circuits provided corresponding to the plurality of sub arrays, each sub phase adjusting and summing circuit performing a sub phase adjusting and summing process with respect to a plurality of group receiving signals to output a sub phase adjusted and summed signal; and at least one main phase adjusting and summing circuit for performing a main phase adjusting and summing process with respect to a plurality of sub phase adjusted and summed signals output from the plurality of sub pbase adjusting and summing circuits;

the array transducer, the group setting section, and the plurality of sub phase adjusting and summing circuits are provided within the probe unit; and the at least one main phase adjusting and summing circuit is provided within the apparatus body.

2. An ultrasound diagnosis apparatus according to claim 1 wherein
the switching circuit is a switching matrix circuit for selectively connecting a plurality of transducer elements within each sub array with a plurality of group signal lines, the switching matrix circuit connecting each transducer element within each sub array to a group signal line selected from the plurality of group signal lines, and the switching matrix circuit being capable of connecting a desired number of transducer elements to each group signal line.

3. An ultrasound diagnosis apparatus according to claim 2, wherein
the switching matrix circuit varies the number of transducer elements connected to each group signal line in accordance with the bean, forming condition.

4. An ultrasound diagnosis apparatus according to claim 2, wherein
a plurality of transducer elements forming each sub array are classified into a plurality of effective transducer elements and one or a plurality of ineffective transducer elements in accordance with the beam forming condition, and the plurality of effective transducer elements are connected with the plurality of group signal lines.

5. An ultrasound diagnosis apparatus according to claim 1, wherein
the receiver section further includes a plurality of main phase adjusting and summing circuits, and
a plurality of receiving beams are simultaneously formed by one receiving process.

6. An ultrasound diagnosis apparatus according to claim 1, wherein
the group setting section includes:
a plurality of switching circuits which are provided corresponding to the plurality of sub arrays, each switching circuit grouping m transducer elements within each sub array into n (1<n <m) groups.

7. An ultrasound diagnosis apparatus according to claim 1, wherein
the group setting section dynamically changes a group setting pattern for each sub array in accordance with a beam scanning direction given as the beam forming condition.

8. An ultrasound diagnosis apparatus according to claim 7, wherein
the change of a group setting pattern includes a change in the number of transducer elements forming each group and a change in a shape of each group.

9. An ultrasound diagnosis apparatus according to claim 8, wherein
the change of a group setting pattern further includes a change in whether or not one or a plurality of ineffective transducer elements are included in each sub array.

10. An ultrasound diagnosis apparatus according to claim 7, wherein
the group setting section sets the group setting pattern for each sub array in accordance with a position in which the sub array is arranged.

11. An ultrasound diagnosis apparatus according to claim 1, wherein
The probe unit includes a probe head; and
the array transducer, the group setting section, and the plurality of sub phase adjusting and summing circuits are provided within the probe head.

12. An ultrasound diagnosis apparatus according to claim 11, wherein
the transmitter section is further provided within the probe head.

13. An ultrasound diagnosis apparatus according to claim 1, wherein
the probe unit includes a probe head, a probe cable connected to the probe head, and a cable connector connected to the probe cable;
the array transducer and the group setting section are provided within the probe head; and
the plurality of sub phase adjusting and summing circuits are provided within the cable connector.

14. An ultrasound diagnosis apparatus according to claim 13, wherein
the transmitter section is further provided within the cable connector.

* * * * *